United States Patent
Abdul-Hafiz et al.

(10) Patent No.: US 8,588,880 B2
(45) Date of Patent: Nov. 19, 2013

(54) EAR SENSOR

(75) Inventors: Yassir Abdul-Hafiz, Irvine, CA (US); Ammar Al-Ali, San Juan Capistrano, CA (US); Kevin Forrest, Rancho Santa Margarita, CA (US); Eugene Mason, La Habra Heights, CA (US); John Schmidt, Huntington Beach, CA (US); Virginia Thanh Ta, Santa Ana, CA (US)

(73) Assignee: Masimo Corporation, Irvine, CA (US)

( * ) Notice: Subject to any disclaimer, the term of this patent is extended or adjusted under 35 U.S.C. 154(b) by 805 days.

(21) Appl. No.: 12/658,872

(22) Filed: Feb. 16, 2010

(65) Prior Publication Data
US 2010/0217103 A1    Aug. 26, 2010

Related U.S. Application Data

(60) Provisional application No. 61/152,964, filed on Feb. 16, 2009.

(51) Int. Cl.
*A61B 5/1455* (2006.01)

(52) U.S. Cl.
USPC ............................ 600/344; 600/322; 600/310

(58) Field of Classification Search
USPC .................................................. 600/309–344
See application file for complete search history.

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Polczynski |
| 5,337,744 A | 8/1994 | Branigan |
| 5,341,805 A | 8/1994 | Stavridi et al. |
| 5,377,676 A | 1/1995 | Vari et al. |
| 5,452,717 A | 9/1995 | Branigan et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |

(Continued)

FOREIGN PATENT DOCUMENTS

GB         191409166         7/1914

OTHER PUBLICATIONS

PCT International Search Report; PCT/US2010/033796; Date of Mailing Oct. 17, 2011; pp. 1-4.

*Primary Examiner* — Eric Winakur
*Assistant Examiner* — Marjan Fardanesh
(74) *Attorney, Agent, or Firm* — Knobbe Martens Olson & Bear, LLP

(57) ABSTRACT

An ear sensor provides a sensor body having a base, legs extending from the base and an optical housing disposed at ends of the legs opposite the base. An optical assembly is disposed in the housing. The sensor body is flexed so as to position the housing over a concha site. The sensor body is unflexed so as to attach the housing to the concha site and position the optical assembly to illuminate the concha site. The optical assembly is configured to transmit optical radiation into concha site tissue and receive the optical radiation after attenuation by pulsatile blood flow within the tissue.

22 Claims, 31 Drawing Sheets

(56) References Cited

U.S. PATENT DOCUMENTS

| | | |
|---|---|---|
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |

(56) References Cited

U.S. PATENT DOCUMENTS

| | | |
|---|---|---|
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,263,396 B2 | 8/2007 | Chen et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 2007/0078315 A1* | 4/2007 | Kling et al. .................. 600/323 |
| 2009/0275813 A1 | 11/2009 | Davis |

* cited by examiner

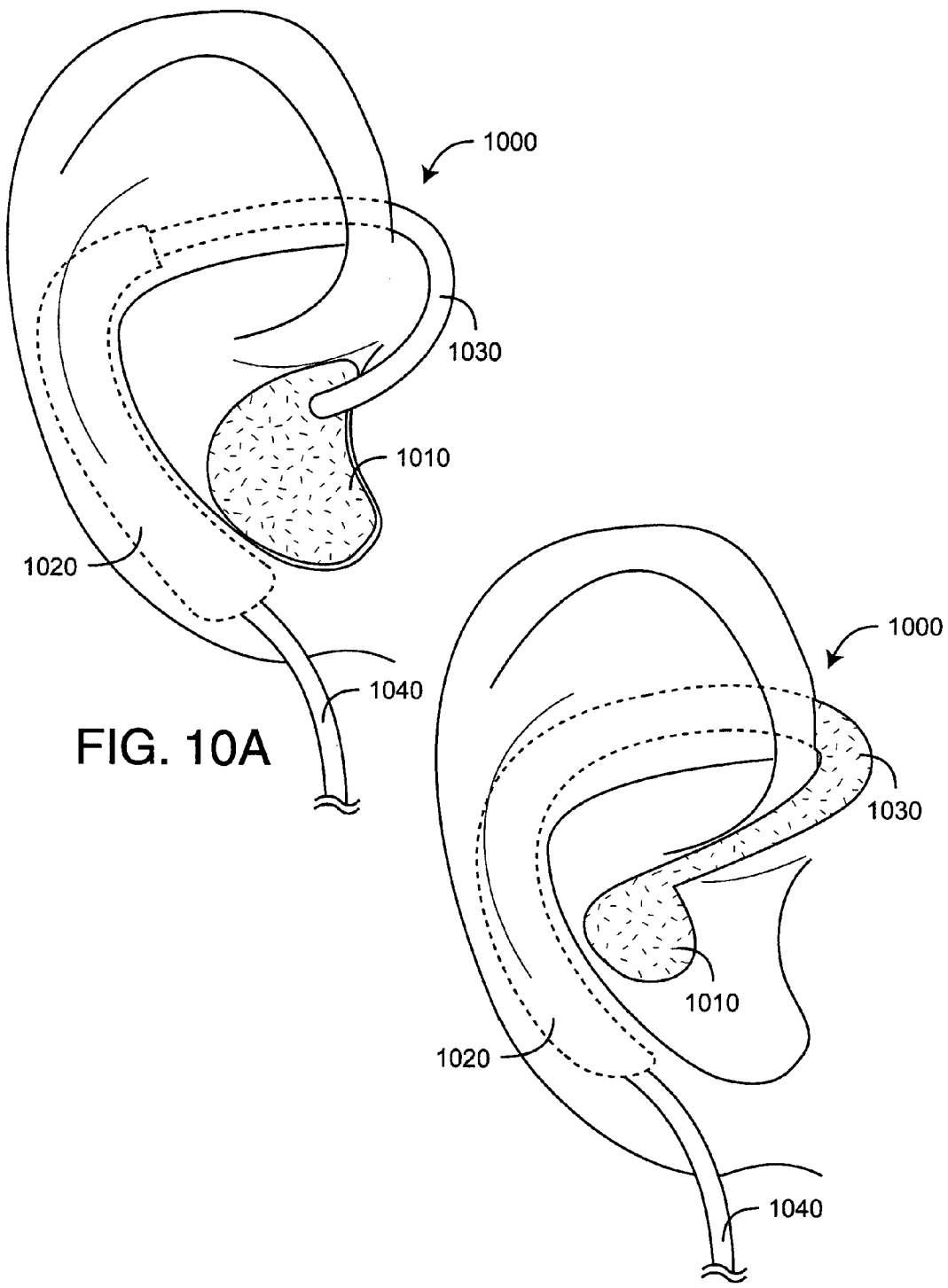

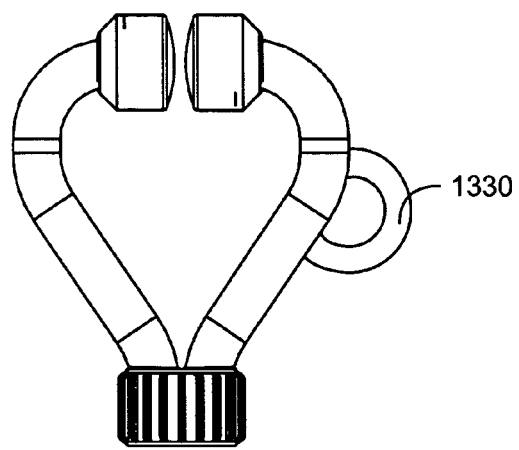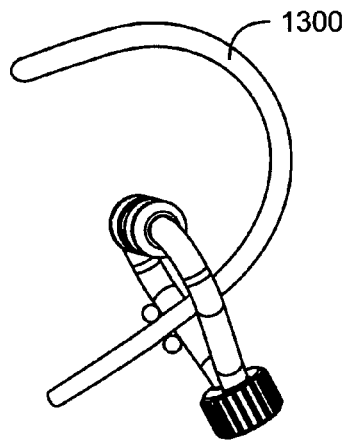
FIG. 13D  FIG. 13E
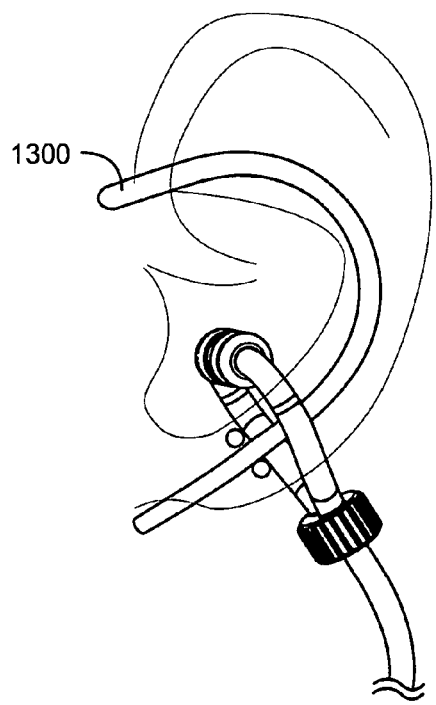
FIG. 13F

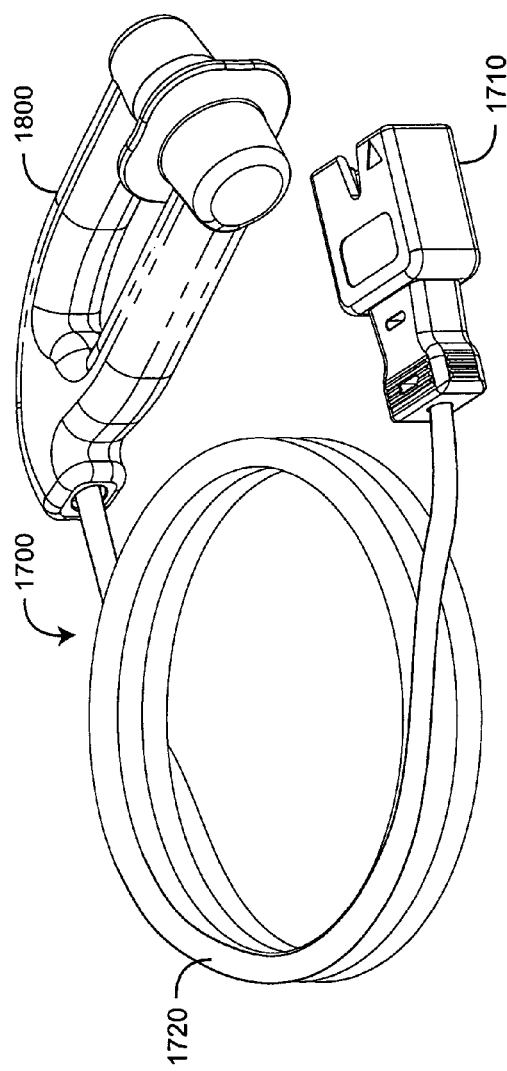
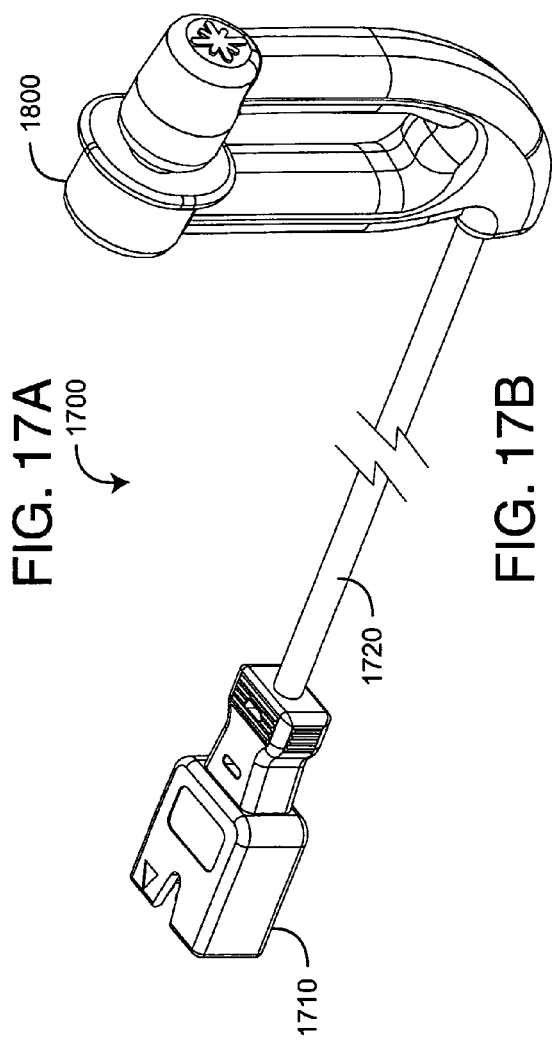
FIG. 17A
FIG. 17B

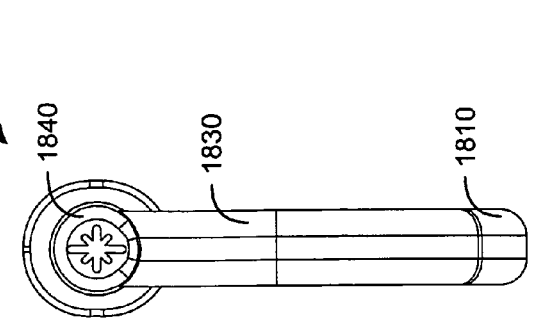
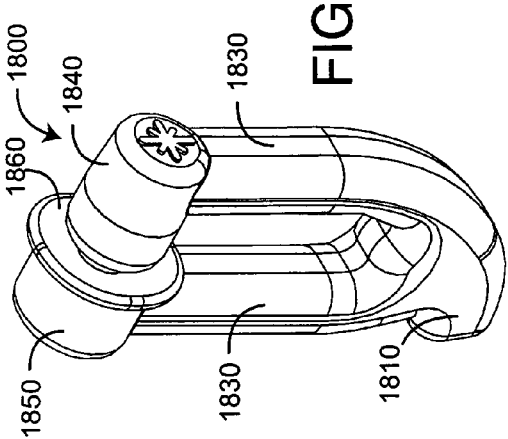
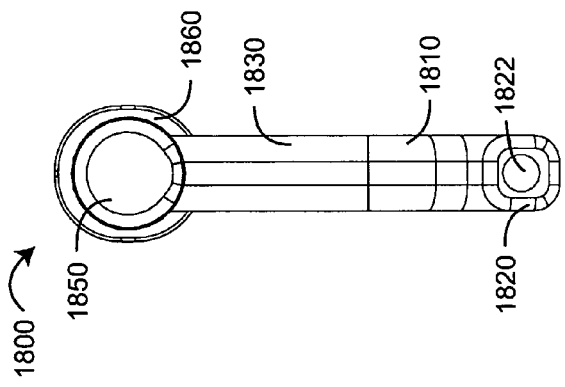
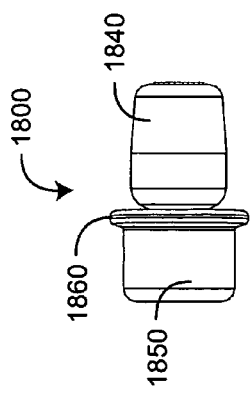
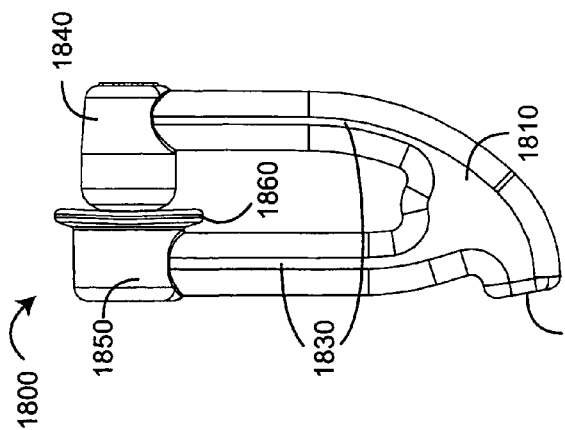

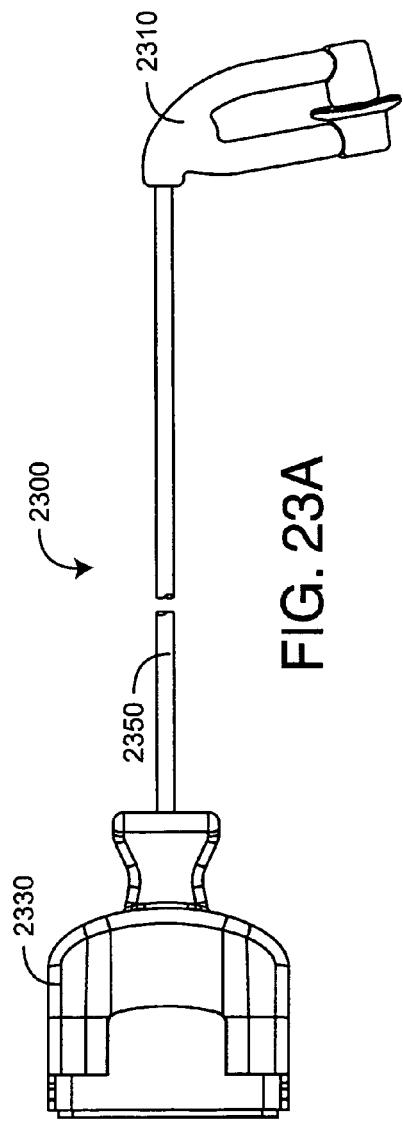
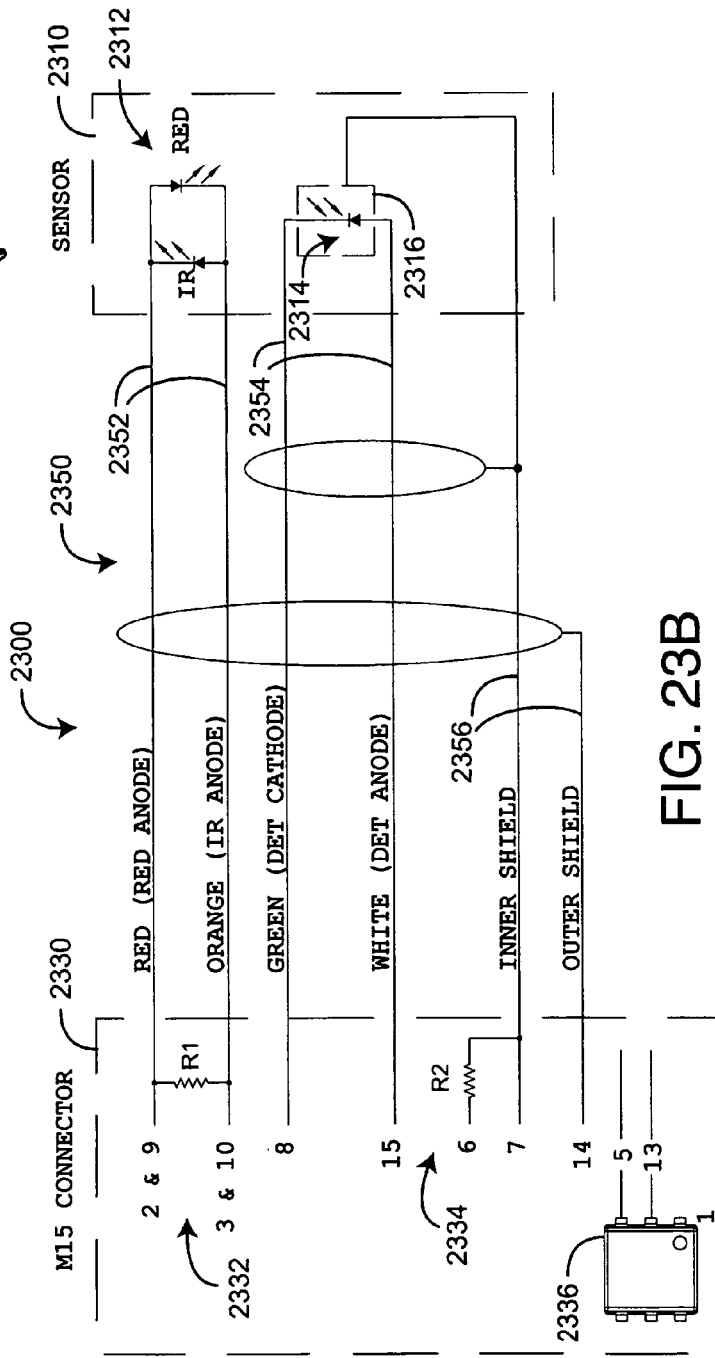
FIG. 23A
FIG. 23B

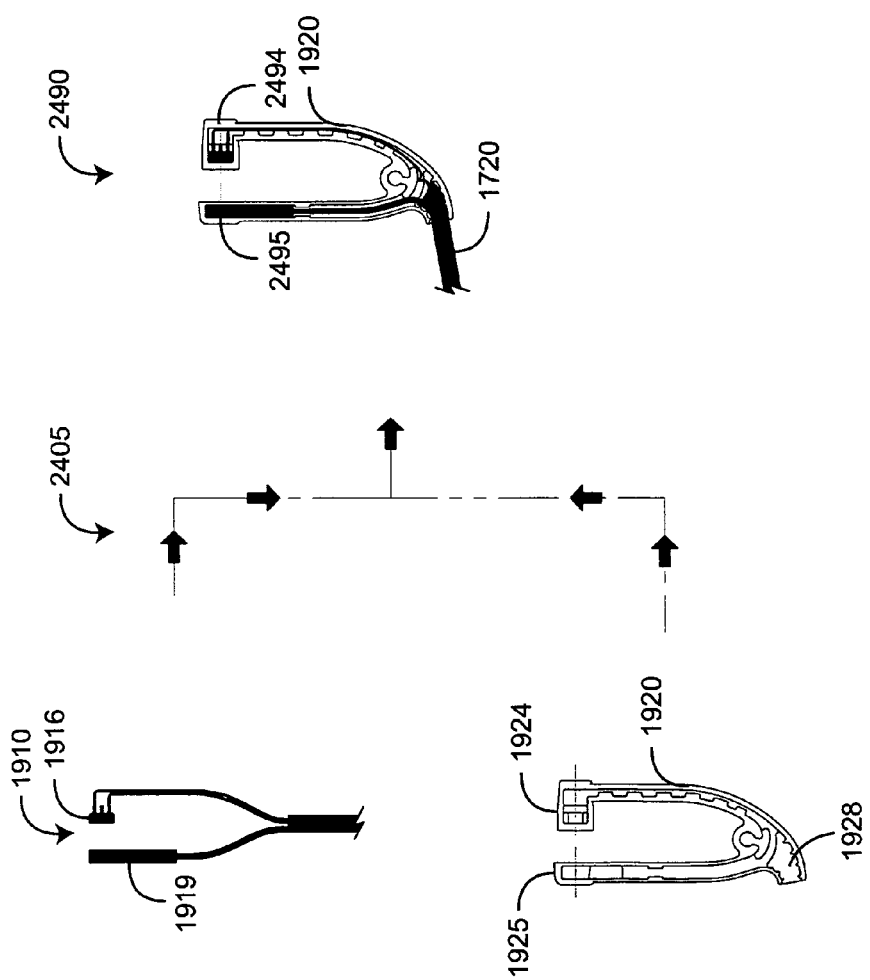

FIG. 25D
SECTION A-A
2550
2525
2520

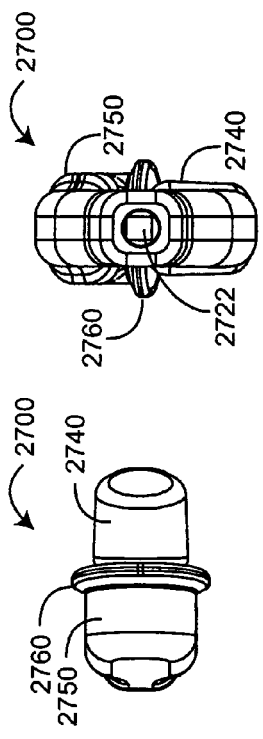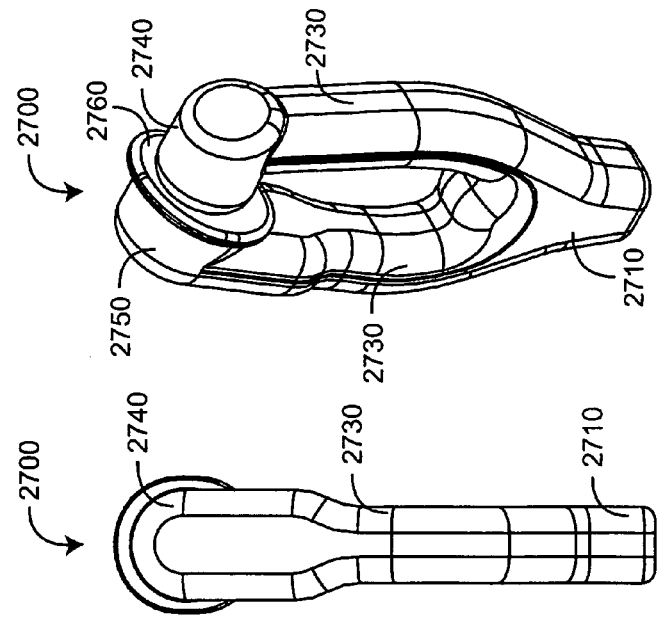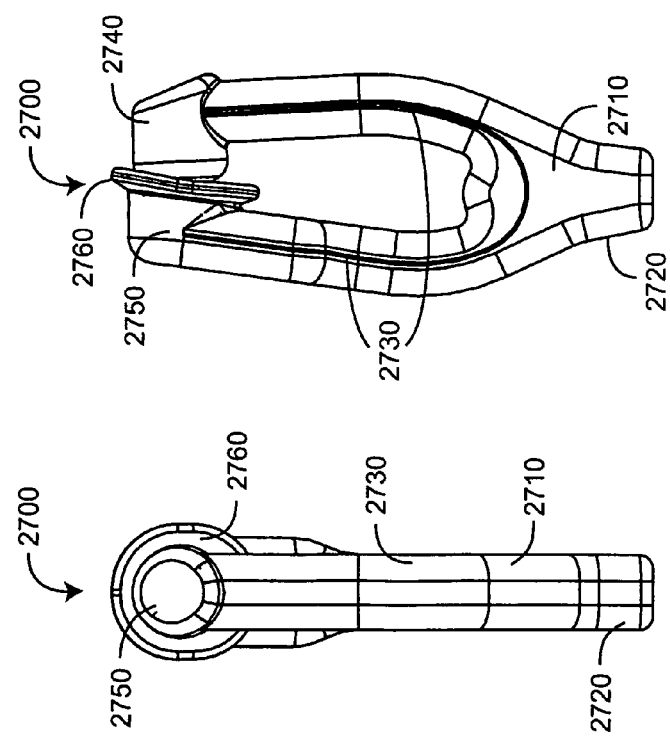

EAR SENSOR

CROSS-REFERENCE TO RELATED APPLICATIONS

The present application claims priority benefit under 35 U.S.C. §119(e) to U.S. Provisional Patent Application Ser. No. 61/152,964, filed Feb. 16, 2009, titled Ear Sensor, hereby incorporated by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation ($SpO_2$) and pulse rate.

Pulse oximeters capable of reading through motion induced noise are disclosed in at least U.S. Pat. Nos. 6,770,028, 6,658,276, 6,650,917, 6,157,850, 6,002,952, 5,769,785, and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein. An ear sensor is disclosed in U.S. Pat. No. 7,341,559 titled Pulse Oximetry Ear Sensor, also assigned to Masimo and also incorporated by reference herein.

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. Advanced physiological monitors and corresponding multiple wavelength optical sensors capable of measuring parameters in addition to $SpO_2$, such as HbCO, HbMet and Hbt are described in at least U.S. patent application Ser. No. 12/056,179, filed Mar. 26, 2008, titled Multiple Wavelength Optical Sensor and U.S. patent application Ser. No. 11/366,208, filed Mar. 1, 2006, titled Noninvasive Multi-Parameter Patient Monitor, both incorporated by reference herein. Further, noninvasive blood parameter monitors and corresponding multiple wavelength optical sensors, such as Rainbow™ adhesive and reusable sensors and RAD-57™ and Radical-7™ monitors for measuring $SpO_2$, pulse rate, perfusion index (PI), signal quality (SiQ), pulse variability index (PVI), HbCO and HbMet among other parameters are also available from Masimo.

SUMMARY OF THE INVENTION

FIG. 1 illustrates various areas of the ear 100 that are amenable to blood parameter measurements, such as oxygen saturation ($SpO_2$). An ear site has the advantage of more quickly and more accurately reflecting oxygenation changes in the body's core as compared to peripheral site measurements, such as a fingertip. Conventional ear sensors utilize a sensor clip on the ear lobe 110. However, significant variations in lobe size, shape and thickness and the general floppiness of the ear lobe render this site less suitable for central oxygen saturation measurements than the concha 120 and the ear canal 130. Disclosed herein are various embodiments for obtaining noninvasive blood parameter measurements from concha 120 and ear canal 130 tissue sites.

One aspect of an ear sensor optically measures physiological parameters related to blood constituents by transmitting multiple wavelengths of light into a concha site and receiving the light after attenuation by pulsatile blood flow within the concha site. The ear sensor comprises a sensor body, a sensor connector and a sensor cable interconnecting the sensor body and the sensor connector. The sensor body comprises a base, legs and an optical assembly. The legs extend from the base to detector and emitter housings. An optical assembly has an emitter and a detector. The emitter is disposed in the emitter housing and the detector is disposed in the detector housing. The legs have an unflexed position with the emitter housing proximate the detector housing and a flexed position with the emitter housing distal the detector housing. The legs are moved to the flexed position so as to position the detector housing and emitter housing over opposite sides of a concha site. The legs are released to the unflexed position so that the concha site is grasped between the detector housing and emitter housing.

In various embodiments, the ear sensor has a resilient frame and a one piece molded skin disposed over the resilient frame. A cup is disposed proximate the detector housing and has a surface that generally conforms to the curvature of the concha site so as to couple the detector to the concha site and so as to block ambient light. A sensor cable has wires extending from one end of the sensor cable and disposed within channels defined by the resilient frame. The wires electrically and mechanically attach to the optical assembly. A connector is attached to the other end of the sensor cable, and the cable wires electrically and mechanically attach to the connector so as to provide communications between the connector and the optical assembly.

In other embodiments, a stabilizer maintains the position of the detector housing and the emitter housing on the concha site. The stabilizer may have a ring that encircles the legs. The ring has a hold position disposed against the legs and a release position spaced from the legs. A release, when pressed, moves the ring from the hold position to the release position, allowing the ring to slidably move along the legs in a direction away from the base so as to increase the force of the emitter housing and detector housing on the concha site in the hold position and in a direction toward the base so as to decrease the force of the emitter housing and the detector housing on the concha site in the hold position. The stabilizer may have an ear hanger that rests along the back of the ear and couples to at least one of the legs and the sensor cable.

Another aspect of an ear sensor comprises providing a sensor body having a base, legs extending from the base and an optical housing disposed at ends of the legs distal the base. An optical assembly is disposed in the housing. The sensor body is flexed so as to position the housing over a concha site. The sensor body is unflexed so as to attach the housing to the concha site and position the optical assembly to illuminate the concha site.

In various embodiments, an ear surface conforming member is molded to at least a portion of the housing so as to physically couple the housing to the concha site and block ambient light from the optical assembly accordingly. The force of the housing against the concha site is adjusted. The adjusting comprises positioning a force adjustment ring on the sensor body so as to encircle the legs. The positioning comprises squeezing a ring release so as to move ring grips away from the legs, moving the force adjustment ring along the legs and toward the housing so as to increase the force of the housing on the concha site, and moving the force adjustment ring along the legs and away from the housing so as to decrease the force of the housing on the concha site.

In other embodiments, an aspect of the ear sensor comprises supporting at least a portion of the weight of the sensor body and corresponding sensor cable so as to reduce the force needed to attach the housing to the concha site. The supporting comprises attaching at least one of the sensor body and sensor cable to an ear hook placed over the ear.

A further aspect of an ear sensor comprising a clip means having a flexed position and an unflexed position. An optical means transmits multiple wavelength light into a tissue site when activated and receives the light after attenuation by pulsatile blood flow within the tissue site. The optical means is disposed on the clip means so that the optical means can be positioned on a concha site in the flexed position and pinched against the concha site in the unflexed position. A connector means mechanically attaches to and electrically communicates with a monitor. A cable means interconnects the connector means with the optical means. In various embodiments, the clip means comprises a resilient frame means for securing the optical means in a fixed position relative to the tissue site. A housing means encloses the resilient frame means and the optical means. A cup means physically couples at least a portion of the optical means to the concha site and blocks ambient light from the optical means. An adjustable force means holds the clip means to the concha site. Alternatively, or in addition to, a support means holds the clip means to the concha site.

BRIEF DESCRIPTION OF THE DRAWINGS

FIGS. 2-3 illustrate various ear sensor embodiments;

FIGS. 4-7 illustrate various ear bud/pad attachment embodiments for a concha site;

FIGS. 8-10 illustrate various "hearing aid" style ear sensor embodiments that integrate the ear sensor with an attachment mechanism;

FIGS. 10A-B illustrate "behind-the-ear" transmissive and/or reflective sensor embodiments;

FIGS. 11-12 illustrate additional integrated ear sensor and attachment embodiments;

FIGS. 13-16 illustrate various ear sensor attachment support embodiments;

FIGS. 13A-F are side views of ear-hook support embodiments;

FIG. 16 is a perspective view of a "headphone" support embodiment;

FIGS. 17-27 illustrate a concha-clip sensor embodiment having an orthogonally-routed sensor cable;

FIGS. 17A-B are perspective views of a concha-clip sensor;

FIGS. 18A-E are top, perspective, front, detector-side and emitter-side views, respectively, of a concha-clip sensor body;

FIG. 19 is an exploded view of an concha-clip sensor;

FIG. 23A-B are a mechanical representation and a corresponding electrical (schematic) representation of a concha-clip sensor having a M15 connector;

FIGS. 24A-C are assembly step representations for installing an optical assembly into a resilient frame and installing the resilient frame into a sensor housing;

FIGS. 25A-E are top, perspective, front, side cross-section; and side views, respectively, of a force adjustment ring;

FIGS. 27A-F are top, bottom, perspective, detector-side, front, emitter side and perspective views, respectively of an concha-clip sensor body having a parallel-routed sensor cable.

DETAILED DESCRIPTION OF THE PREFERRED EMBODIMENTS

Figure 1:
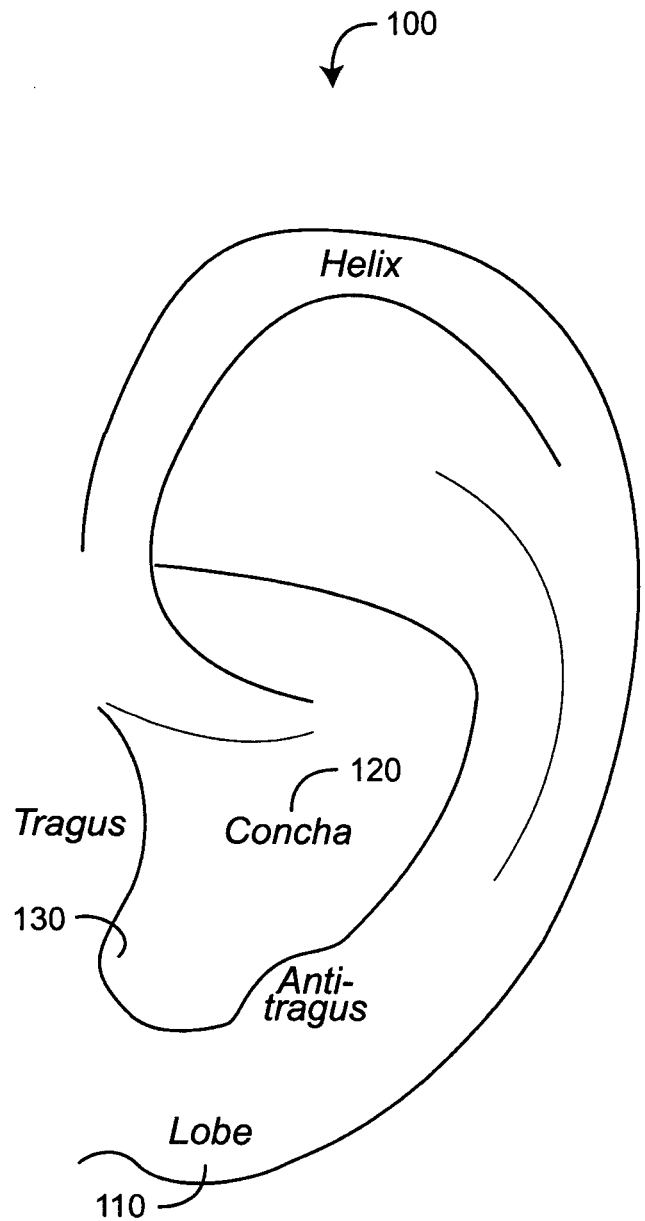
FIG. 1 is an illustration of the pinna or external ear structure, including the concha.
Figure 2A:
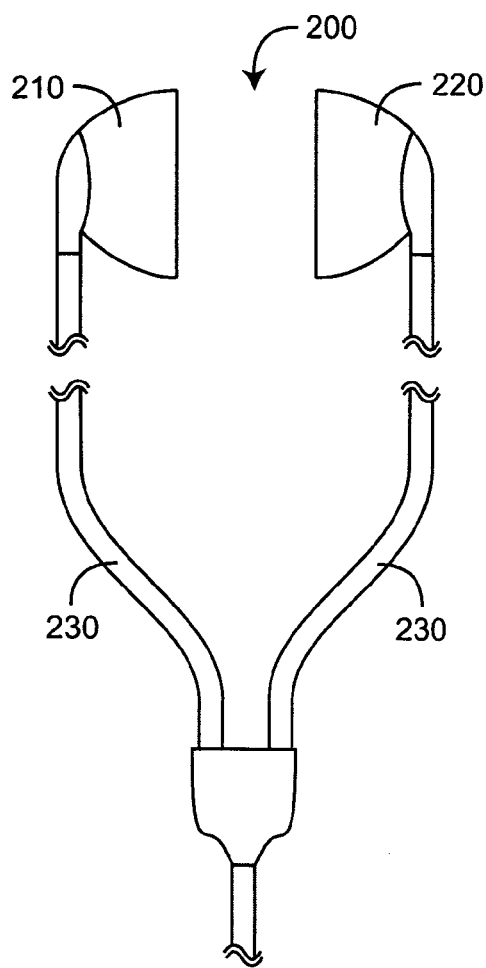
FIGS. 2A-B are a side view and a perspective view of an ear bud embodiment of an ear sensor.
Figure 2B:
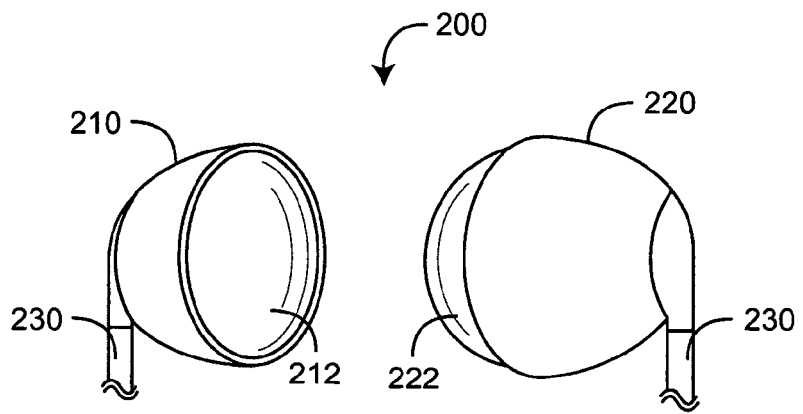

FIGS. 2A-B illustrate an ear bud embodiment of an ear sensor 200 having an emitter ear bud 210, a detector ear bud 220 and connecting cables 230. The emitter ear bud 210 has a generally concave surface for attachment to the back of an ear. The detector ear bud 220 has a generally convex surface 222 for attachment inside the ear at a concha site opposite the emitter ear bud 210. Sensor cables 230 are attached at the back of each ear bud having wires for electrical communications with a physiological monitor, such as a pulse oximeter. In particular, the emitter ear bud 210 includes wires for receiving emitter drive current from a monitor and the detector ear bud 220 includes wires for transmitting photodiode current to the monitor.

Figure 3A:
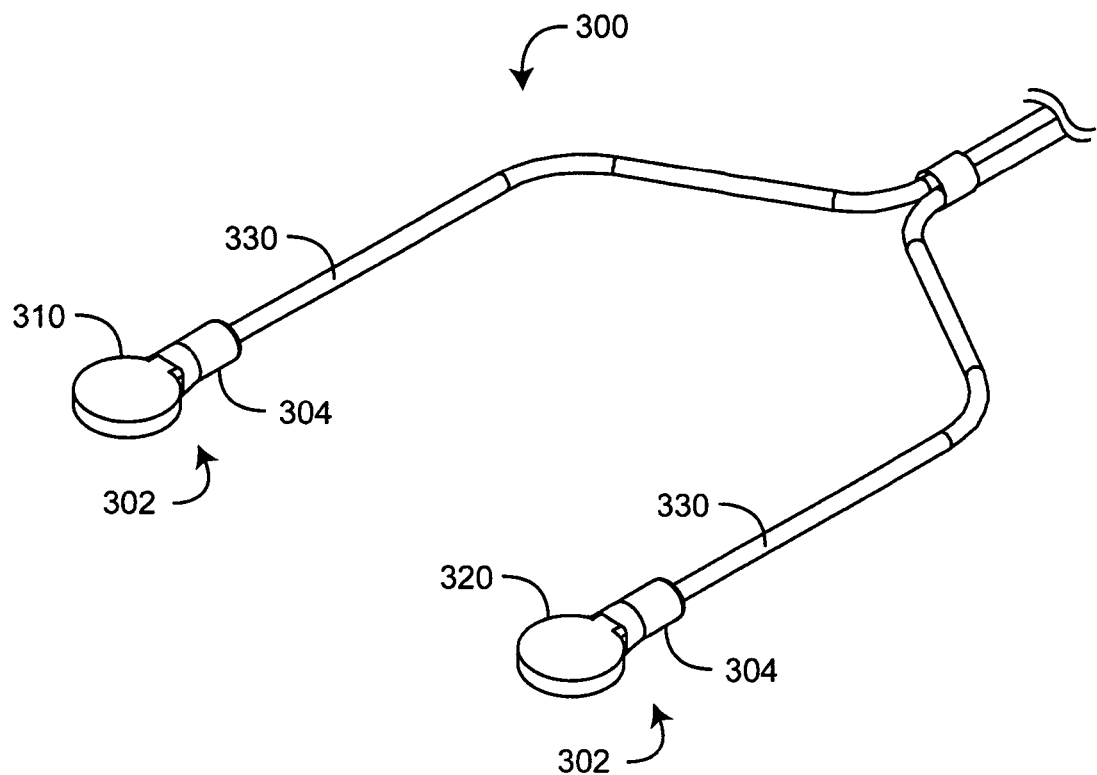
FIGS. 3A-B are perspective views of a flexible ear pad embodiment of an ear sensor.
Figure 3B:
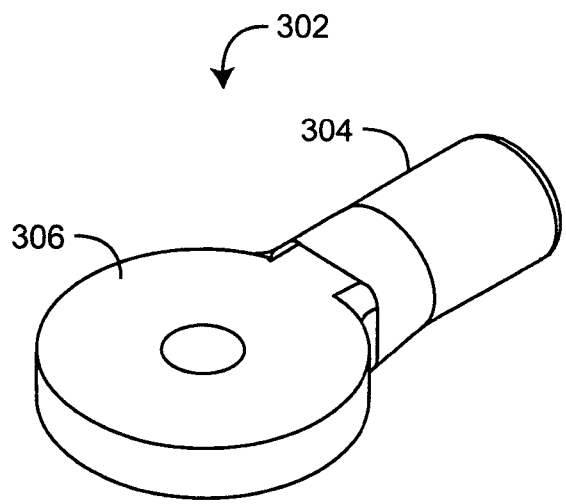

FIGS. 3A-B illustrate a flexible ear pad embodiment of an ear sensor 300 having an emitter pad 310, a detector pad 320 and corresponding cables 330. The sensor pads 310, 320 advantageously include a housing for each of the emitter pad 310 and the detector pad 320, minimizing the number of unique parts for the ear sensor. The detector pad 320 houses a shielded detector assembly (not shown). The emitter pad houses 310 an emitter (not shown). Both the detector pad 320 and the emitter pad 310 are connected to a sensor cable 330. The pads 310, 320 have an integrated bend relief 304 providing a finger grip. The pad face 306 provides a generally planar, pliant contact surface that can adapt to the curved front and back surfaces of a concha site. The pad face 306 has a relatively large area to minimize contact force. The housing 302 is injection molded of a pliant material. In one embodiment, the material is a medical grade thermoplastic elastomer.

FIGS. 2-3, above, illustrate various ear sensor embodiments. Although described with respect to ear bud and flexible ear pad enclosures, the sensor emitter and detector may be enclosed in any number of housings having various sizes and shapes of ear tissue contact surfaces, may use various types of electrical interconnnect and use various materials so as to noninvasively measure blood parameters from the concha area of the ear. As an example, the detector and emitter may both be mounted at one end of a "Y"-shaped flex circuit that has a connector at the opposite end. Although described above with respect to a detector placed inside the ear and an emitter placed outside the ear, a suitable alternative is the emitter inside and the detector outside the ear. Detector and emitter assemblies are described with respect to FIGS. 19-20, below.

FIGS. 4A-D illustrate "C"-clip embodiments 400 for attaching an ear sensor 410 to a concha site. The clip 400 is adapted for use with either the ear bud or the ear pad embodiments described above. The clip 400 has sensor mounts 420 fixedly attached to each end of a flexible "C"-shaped body 422. The body 422 is made of a suitable material having an appropriate stiffness so as to provide a comfortable yet secure attachment to ear tissue. The sensor mounts 420 have mounting apertures sized for the ear buds or ear pads described above. The ear buds or pads are secured within the apertures with a friction fit or adhesive. In an alternative embodiment, the sensor housings are molded or otherwise integrated with the sensor mounts.

Figures 4A, 4B:
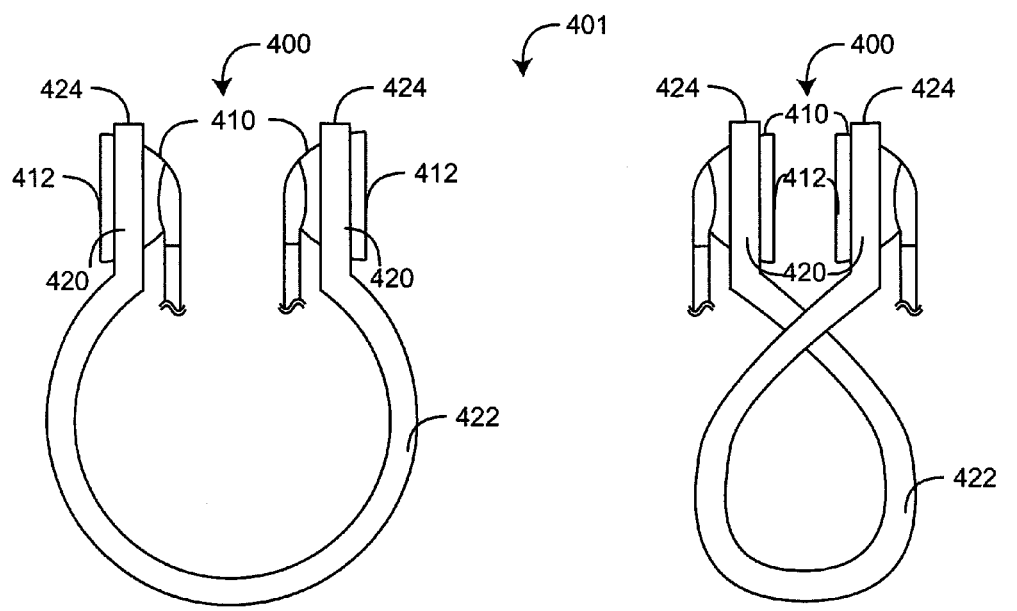
FIGS. 4A-D are side views of "C"-clip embodiments for attaching an ear sensor to a concha site.
Figures 4C, 4D:
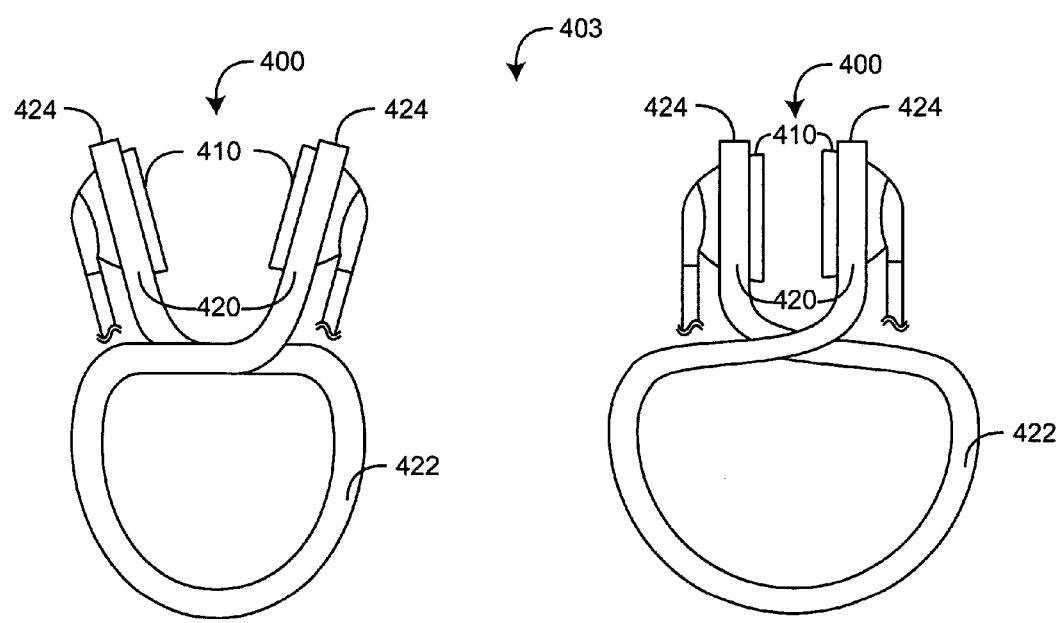

As shown in FIGS. 4A-B, in one embodiment 401 the unflexed clip 400 (FIG. 4A) is compressed between fingertips so that the clip ends 424 are crossed (FIG. 4B) and the contact surfaces of the ear sensor 412 are facing each other. The clip 400 is placed over the ear so that the detector and emitter ear buds are on opposite sides of the ear. Finger pressure on the clip 400 is then released so that the clip tension holds the sensor contact surfaces 412 against the concha tissue. As shown in FIGS. 4C-D, in another embodiment 403 the clip ends 424 are crossed in both the flexed position (FIG. 4C) and the unflexed position (FIG. 4D). Otherwise, sensor attachment is as described above. Although described above as a "C"-shape, the clip body can be constructed of any of various springy, pre-formed materials having a variety of shapes and sizes so as to attach to ear tissue via compression and release between finger and thumb.

Figure 5A:
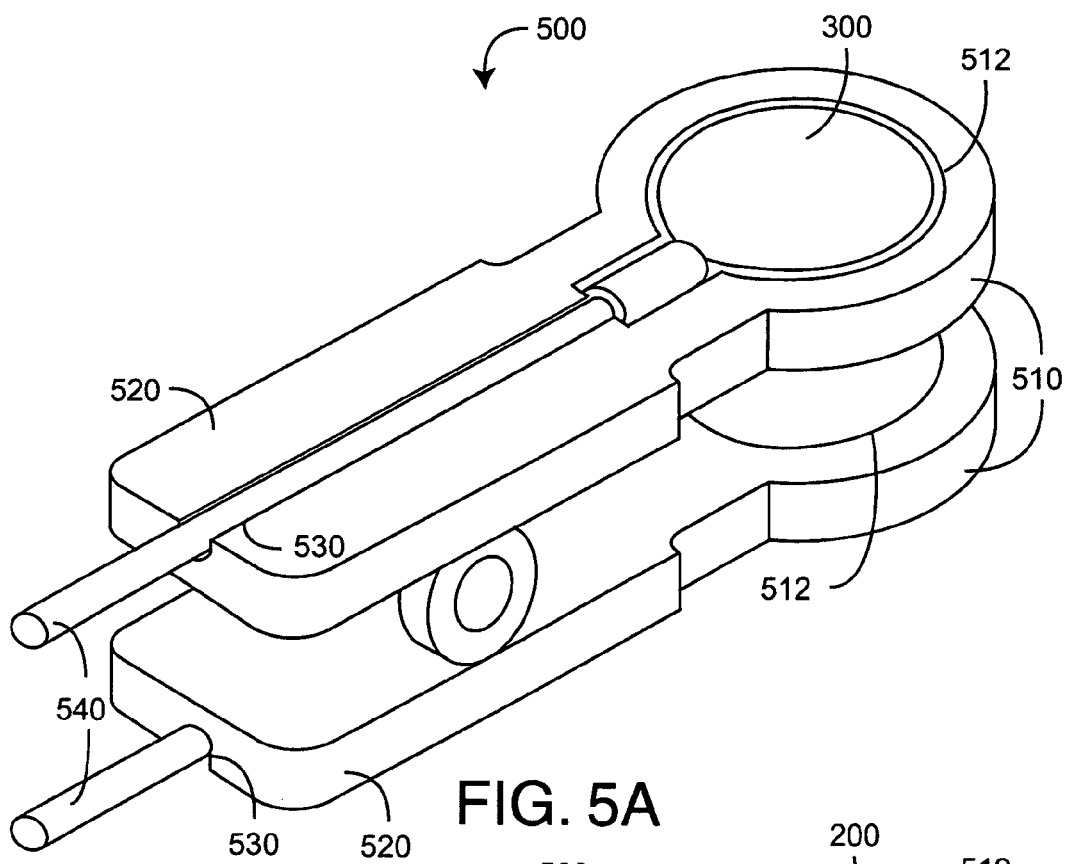
FIGS. 5A-B are perspective views of alligator clip embodiments for attaching an ear sensor to a concha site.
Figure 5B:
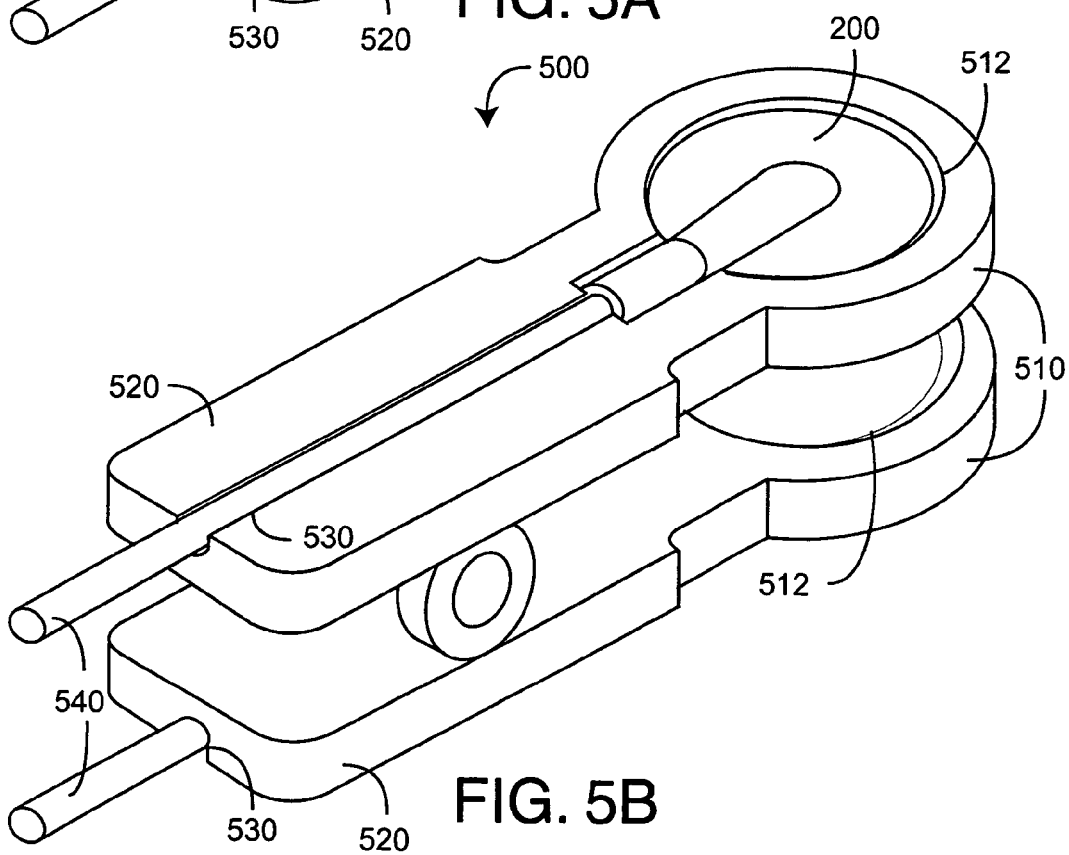

FIGS. 5A-B illustrate an alligator clip embodiment for attaching an ear sensor to a concha site. The alligator clip 500 has opposing heads 510, each with a thru-hole 512 sized to accommodate either an ear pad sensor 300 (FIG. 5A) or an ear bud sensor 200 (FIG. 5B). The alligator clip 500 also has finger grips 520 each with a channel 530 for routing the sensor cabling 540. The alligator clip is compressed and released to position and then attach the corresponding ear sensor to a concha site.

Figure 6A:
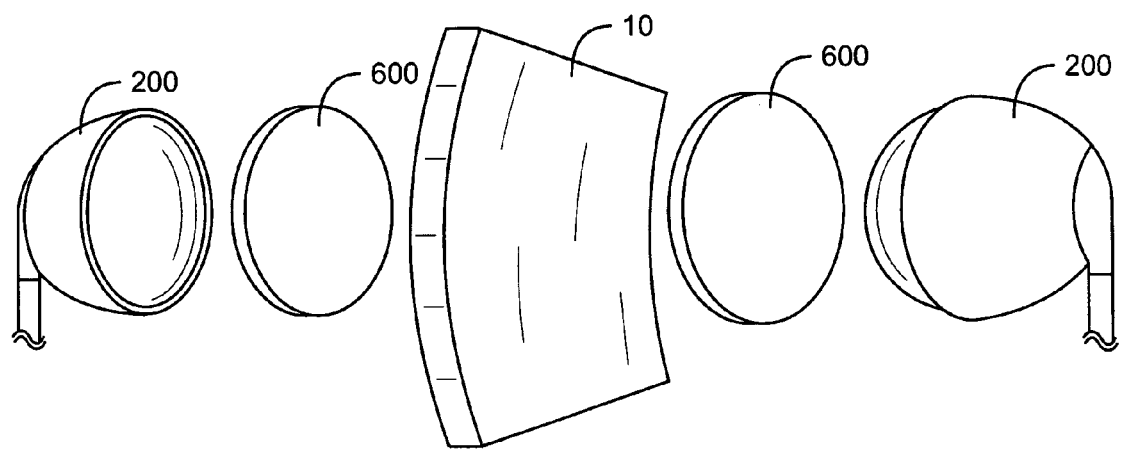
FIGS. 6A-B are perspective views of a clear adhesive disk embodiment for attaching an ear sensor to a concha site.
Figure 6B:
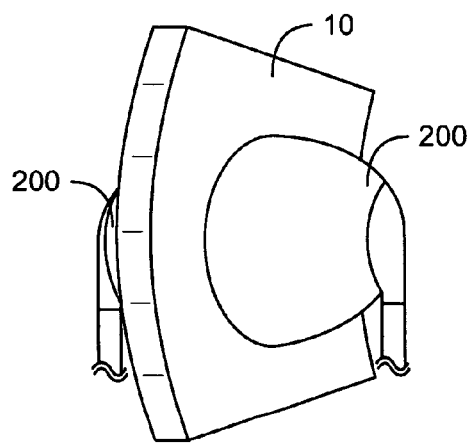

FIGS. 6A-B illustrate an adhesive disk embodiment for attaching an ear sensor to a concha site. Clear disks 600 have an adhesive on both surfaces. The adhesive is bio-compatible on at least the tissue-facing surface. The disks 600 are first attached to the sensor 200 or to a concha site 10. Then the ear sensor 200 is attached on opposite sides of the concha tissue 10. The disks 600 are sized to accommodate either an ear bud sensor 200, as shown, or an ear pad sensor 300 (FIGS. 3A-B).

Figure 7A:
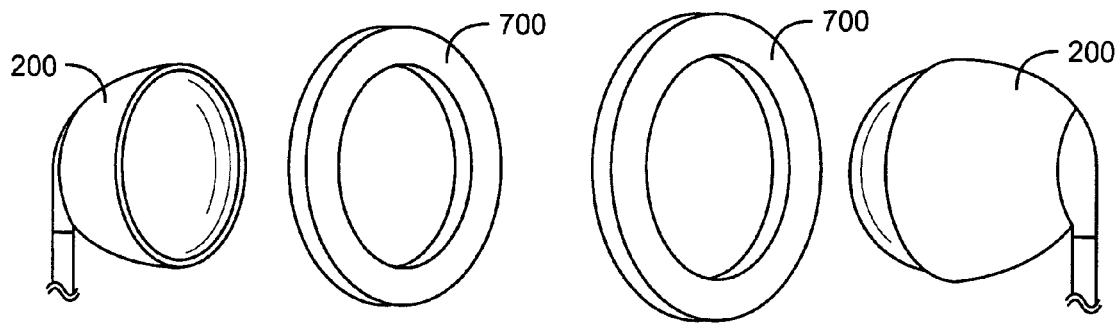
FIGS. 7A-C are perspective views of a flexible magnet disk embodiment for attaching an ear sensor to a concha site.
Figure 7B:
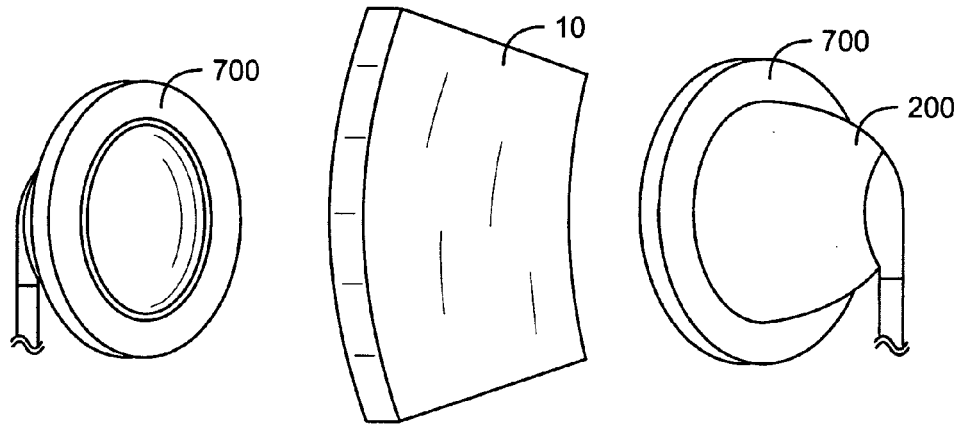
Figure 7C:
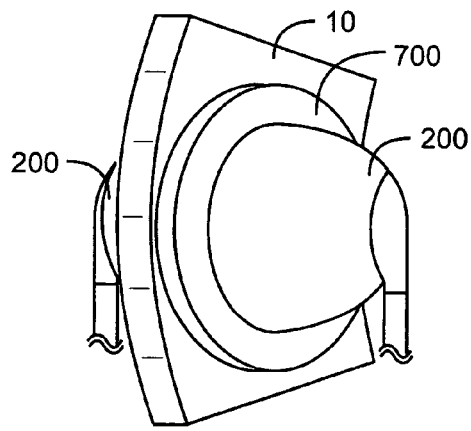

FIGS. 7A-C illustrate a flexible magnet disk embodiment for attaching an ear sensor to a concha site. Flexible magnetic disks 700, such as made from a mixture of a ferrite powder and a rubber polymer resin, are permanently or temporarily attached to an ear sensor 200. The attachment may be by friction fit or a removable or permanent adhesive. The ear sensor 200 is then placed on opposite sides of the concha site 10 and held in place by the magnetic force of the disks. One or both disks may be permanently magnetized during manufacture. The disks 700 are sized to accommodate either the ear bud sensor 200, as shown, or the ear pad sensor 300 (FIGS. 3A-B). In an alternative embodiment, each of the ear sensor housings is at least partially composed of a high magnetic permeable material. One or both of the housings are magnetized. In another embodiment, one or more rare earth magnets are embedded in one or both housings.

FIGS. 4-7, described above, illustrate various ear sensor attachment embodiments. Although described with respect to clips and adhesive or magnetic disks, the sensor emitter and detector may be attached to an ear tissue site using various other materials and mechanisms. For example, ear buds or pads may attach via suction cups or disks. Also, an emitter and detector may be integrated with disposable adhesive pads configured with snaps or other mechanical connectors for attaching and removing sensor leads from the disposable pads. In another embodiment, a sensor may be mounted in the concha or the ear canal using an expanding foam material that is first squeezed and then released after sensor placement within the ear.

Figure 8A:
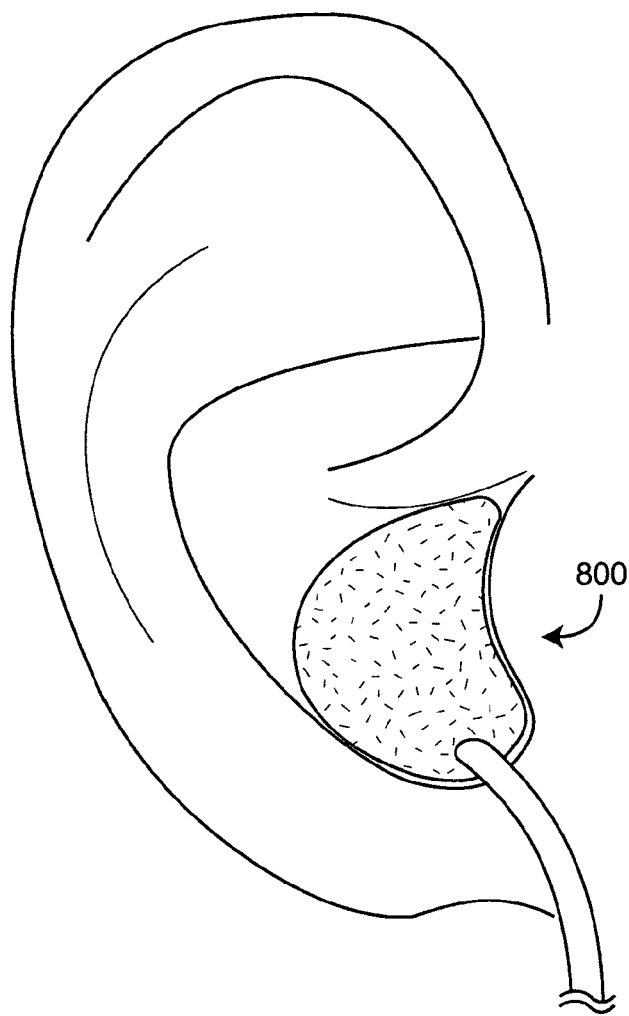
FIGS. 8A-B illustrate a concha-placed reflective sensor embodiment.
Figure 8B:
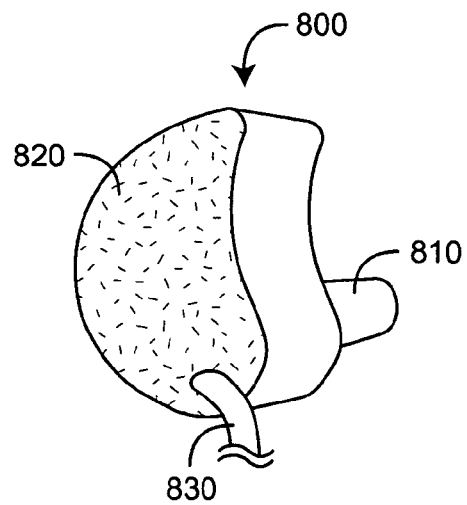

FIGS. 8A-B illustrate a concha-placed reflective sensor embodiment. In one embodiment the sensor 800 has an ear canal extension 810 (FIG. 8B). In an embodiment, the ear canal extension has at least one emitter and at least one detector disposed proximate the extension surface so as to transmit light into ear canal tissue and to detect the transmitted light after attenuation by pulsatile blood flow within the ear canal tissue. In an embodiment, the emitter and detector are axially spaced on the extension. In an embodiment, the emitter and detector are radially spaced on the extension at a fixed angle, which may be, as examples, 30, 45, 90, 120, 135, 160 or 180 degrees.

In an embodiment, the concha-placed sensor body 820 has at least one emitter and at least one detector in lieu of an ear canal extension emitter and detector. The sensor body emitter and detector are disposed proximate the concha surface so as to transmit light into concha tissue and to detect the transmitted light after attenuation by pulsatile blood flow within the concha tissue. In an embodiment, the concha-placed sensor body 820 and the ear canal extension 810 both have at least one emitter and at least one detector, creating a multi-site (concha and ear canal) reflective sensor. Connected with the sensor body 820 is a sensor cable 830 providing electrical communications between sensor body/ear canal emitter(s) and detector(s) and a monitor. Detector and emitter assemblies are described with respect to FIGS. 19-20, below.

Figure 9A:
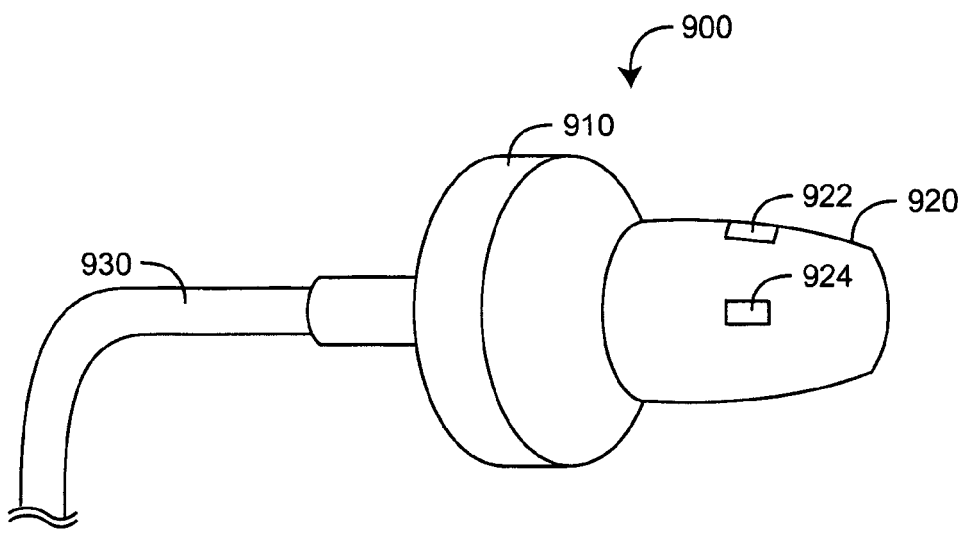
FIGS. 9A-B illustrate an "in-the-canal" reflective sensor embodiment.
Figure 9B:
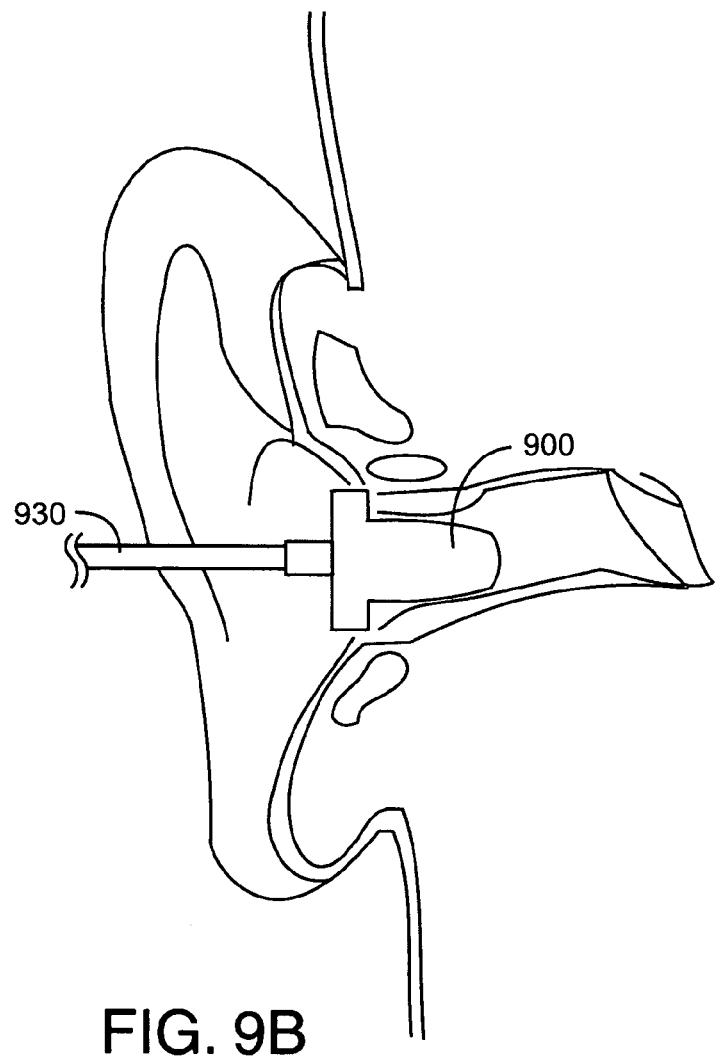

FIGS. 9A-B illustrate an "in-the-canal" ear sensor embodiment. The ear canal sensor 900 has a base 910, an ear canal extension 920 and a sensor cable 930. Similar to the embodiment described above, the ear canal extension 920 has at least one emitter 922 and at least one detector 924 disposed proximate the extension surface so as to transmit light into ear canal tissue and to detect the transmitted light after attenuation by pulsatile blood flow within the ear canal tissue. The emitter 922 and detector 924 may be axially-spaced on the ear canal extension a fixed distance. Alternatively, the emitter and detector may be radially-spaced on the ear canal extension at any of various angles, such as 30, 45, 90, 120, 135, 160 or 180 degrees, to name a few. A sensor cable 930 is attached to the sensor so as to extend from the ear canal to a corresponding monitor.

FIGS. 10A-B illustrate "behind-the-ear" transmissive and/or reflective sensor embodiments. The ear sensor 1000 has a concha-placed body 1010, an ear piece 1020, a connecting piece 1030 attaching the concha body 1010 and the ear piece 1020 and a sensor cable 1040. In one embodiment, a concha-placed body 1010 houses a detector and the ear piece 1020 houses an emitter opposite the detector so as to configure a transmissive concha sensor. In an embodiment, the concha-placed body 1010 or the ear piece 1020 has both an emitter and a detector so as to configure a reflective concha sensor. In an embodiment, the concha body 1010 and the ear piece 1020 are configured for multi-site transmissive and/or reflective concha tissue measurements. In an embodiment, the concha body 1010 also has an ear canal extension (see, e.g. 810 FIG. 8B), which may also have an emitter and detector for multi-site concha and ear canal measurements. A sensor cable 1040 extends from the ear piece 1020 as shown. Alternatively, a sensor cable extends from the concha body, such as shown in FIG. 8B, above.

Figure 11A:
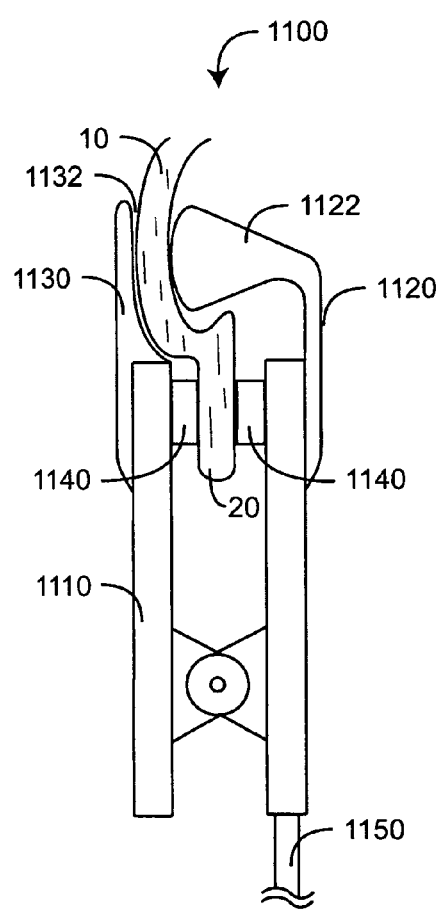
FIGS. 11A-B illustrate an integrated ear lobe attachment and concha-placed sensor embodiment.
Figure 11B:
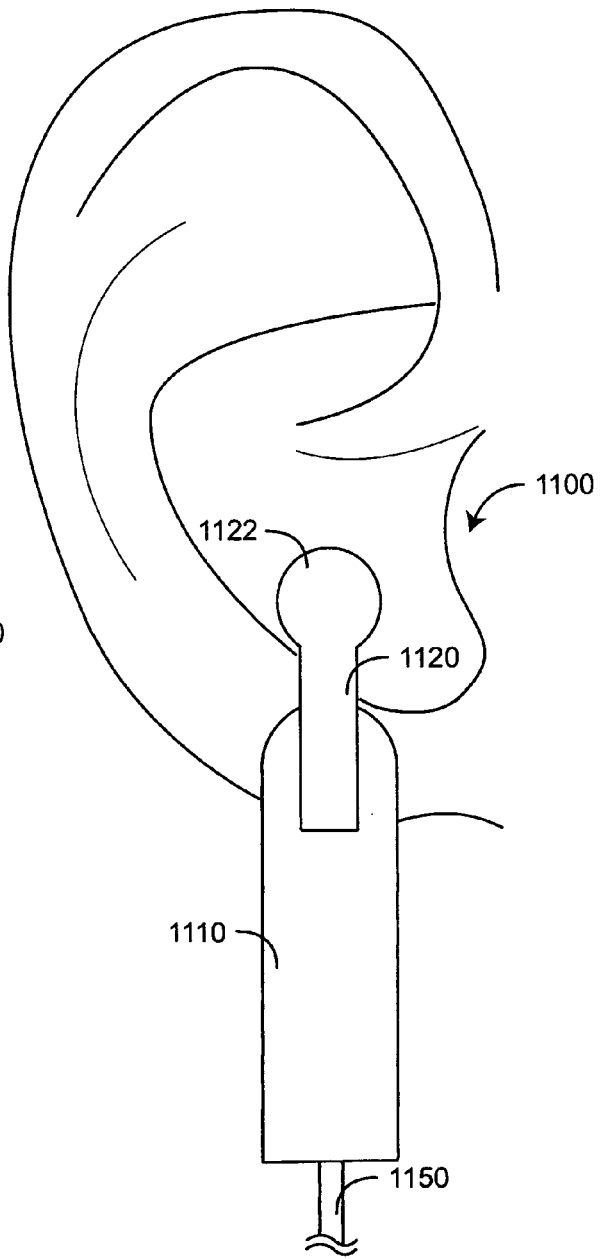
Figure 12A:
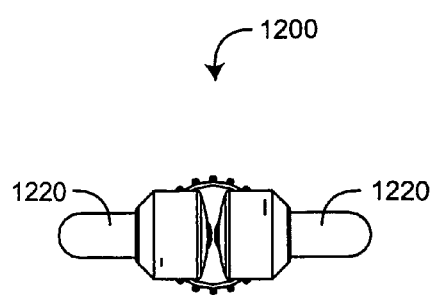
FIGS. 12A-F illustrate a "Y"-clip sensor embodiment for concha-placement.
Figure 12B:
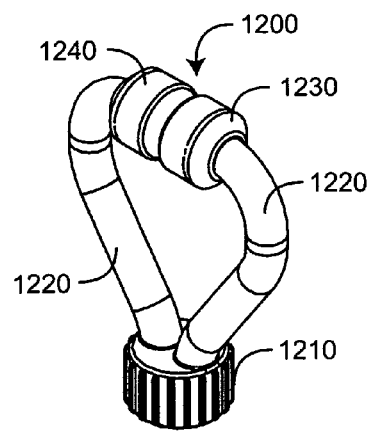
Figure 12C:
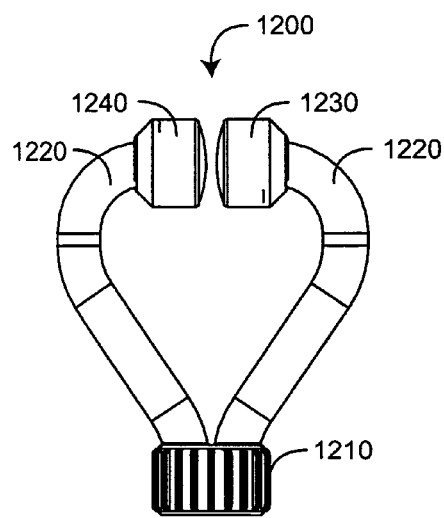
Figure 12D:
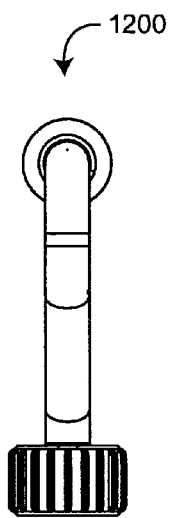
Figure 12E:
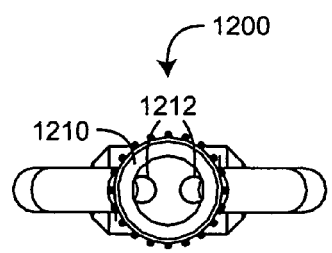
Figure 12F:
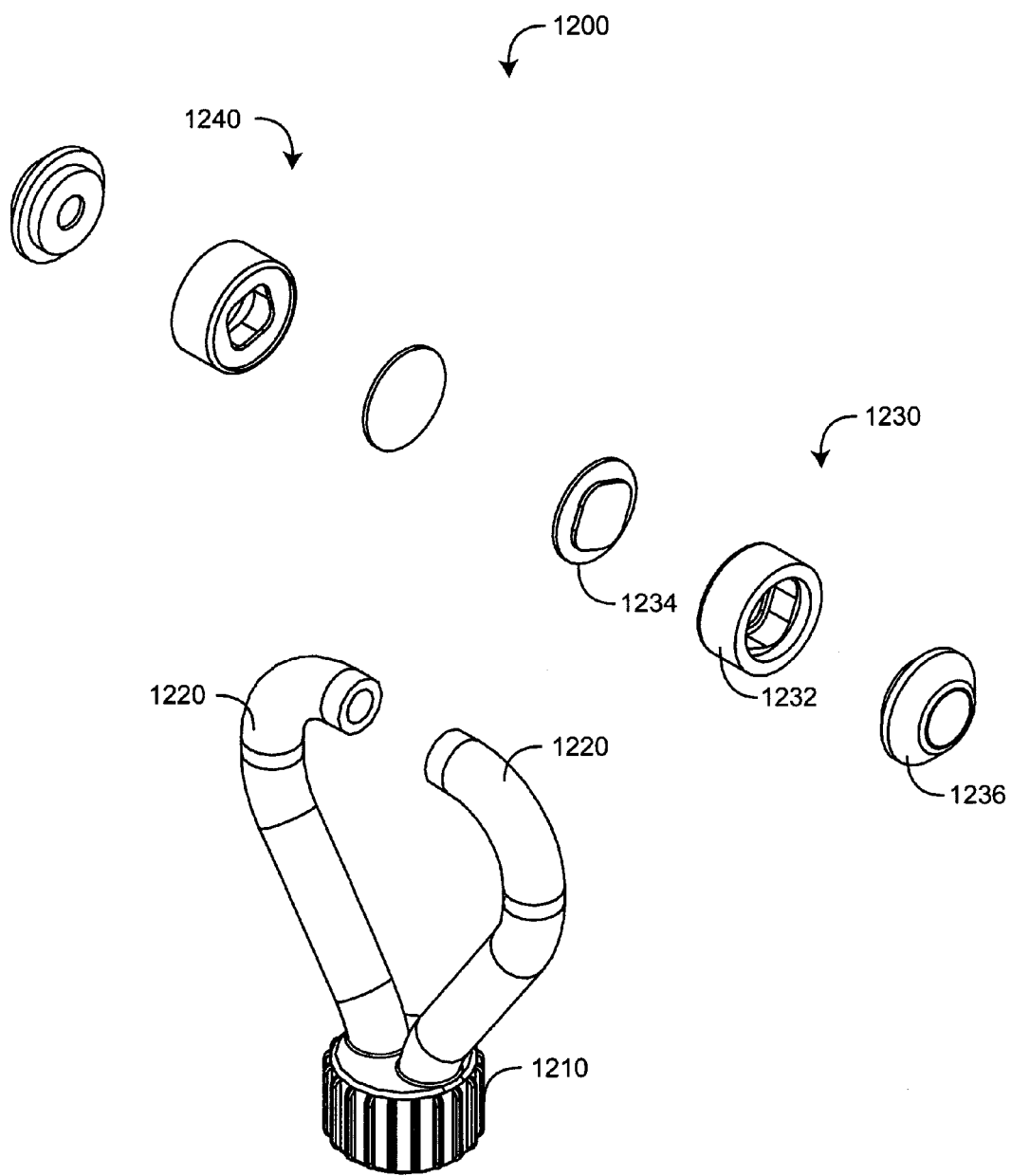
Figure 13A:
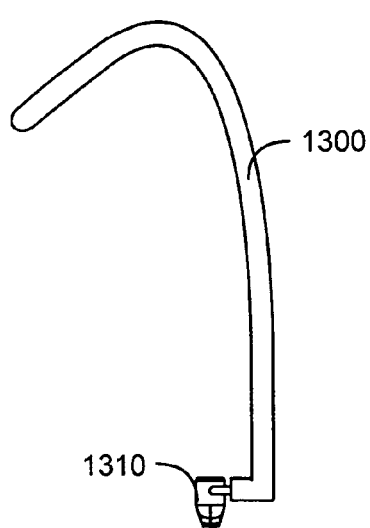
Figure 13B:
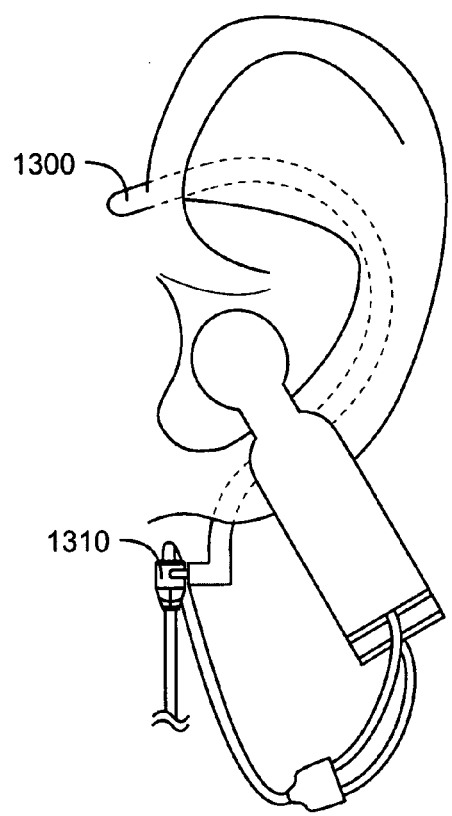
Figure 13C:
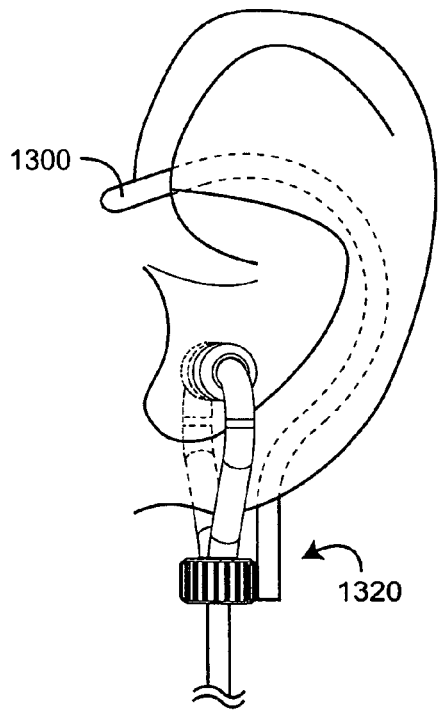

FIGS. 11A-B illustrate a concha sensor 1100 having an alligator clip 1110, a concha piece 1120, a ear back piece 1130, a lobe attachment 1140 and a sensor cable 1150. In an embodiment, the alligator clip 1110 attaches to the ear lobe 20 so as to provide the physical support for a concha sensor 1100. A convex body 1122 extends from the concha piece 1120. A detector disposed at the convex body 1122 surface is disposed against the concha tissue 10. A concave surface 1132 is defined on the back piece 1130 and positioned behind the ear. An emitter disposed at the concave surface 1132 is disposed against the ear wall opposite the concha detector. The concha piece 1120 and ear back piece 1130 are "springy" so as to securely contact the concha tissue 10 under the force of the alligator clip 1110, but without undue discomfort. In an embodiment, the lobe attachment 1140 also has an emitter and detector so as to provide multi-site ear tissue measurements at the ear lobe 20 and the concha 10.

FIGS. 12A-F illustrate a "Y"-clip ear sensor 1200 having a base 1210, a pair of curved clips 1220 extending from the base, an emitter assembly 1230 extending from one clip end and a detector assembly 1240 extending from another clip end. The clips 1220 are tubular so as to accommodate wires from the emitter/detector assemblies, which extend from apertures 1212 in the base. Each assembly has a pad 1232, a molded lens 1234 and a lid 1236, which accommodate either an emitter subassembly or a detector subassembly. The Y-"clips" flex so as to slide over the ear periphery and onto either side of the concha. The integrated emitter and detector, so placed, can then transmit multiple wavelength light into the concha tissue and detect that light after attenuation by pulsatile blood flow within the concha tissue.

FIGS. 13A-F illustrate ear hook sensor support embodiments having an ear hook 1300 with cable 1310, fixed 1320 or sliding 1330 support for either an alligator clip or a "Y"-clip sensor. These embodiments are also applicable to "C"-clip sensors and alligator clip sensors, among others.

Figure 14A:
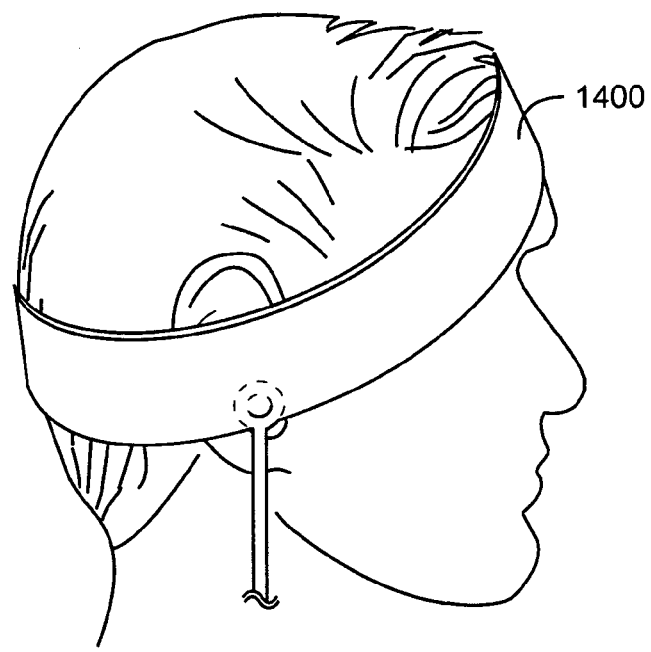
FIGS. 14A-B are perspective views of headband support embodiments.
Figure 14B:
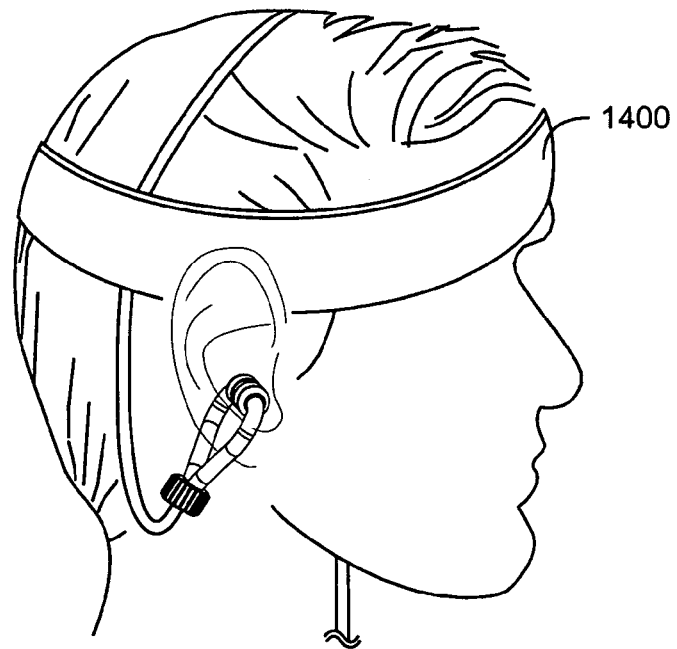

FIGS. 14A-B illustrate headband sensor support embodiments. In one embodiment, the headband 1400 secures a concha body (FIGS. 8A-B) or an ear canal sensor (FIGS. 9A-B) by placement over the ear. In another embodiment, the headband 1400 provides a cable support for an ear clip sensor.

Figure 15A:
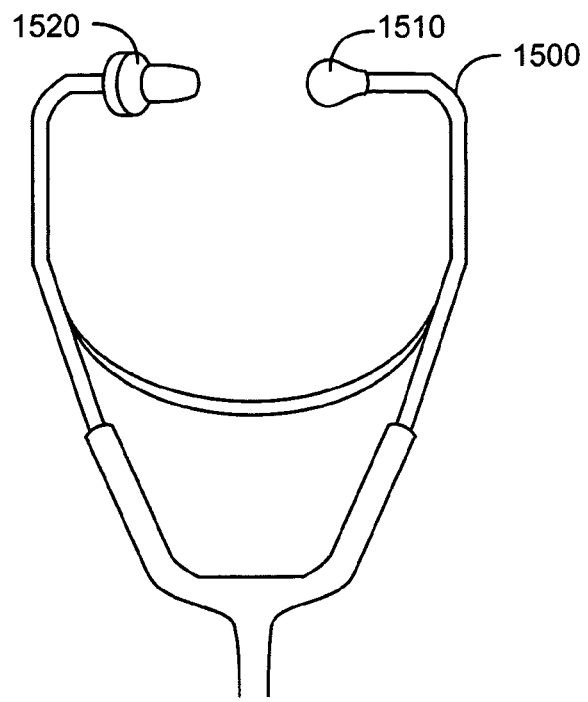
FIGS. 15A-B are front and perspective views of a "stethoscope" support embodiment.
Figure 15B:
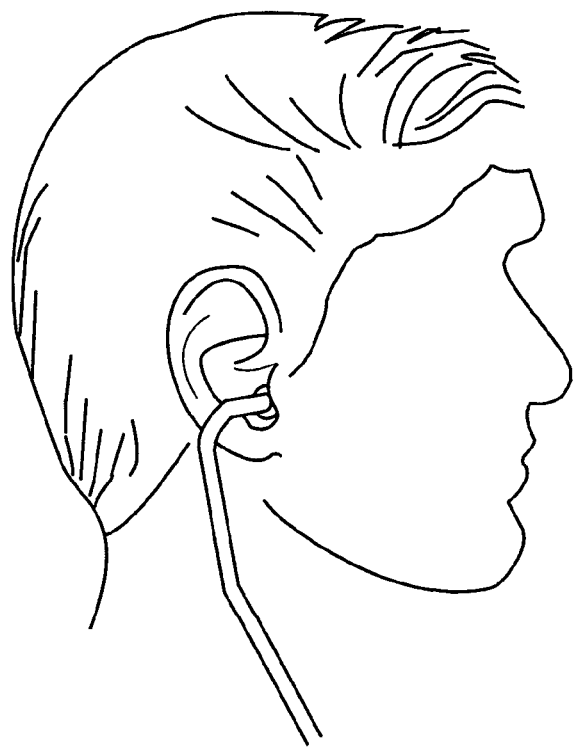

FIGS. 15A-B illustrate a "stethoscope" 1500 sensor support embodiment. In this embodiment, one ear piece 1510 is integrated with an ear canal sensor 1520, such as described above with respect to FIGS. 9A-B. In another embodiment, both stethoscope ear pieces 1510 are integrated with ear canal sensors for multi-site (both ears) blood parameter measurements.

Figure 16:
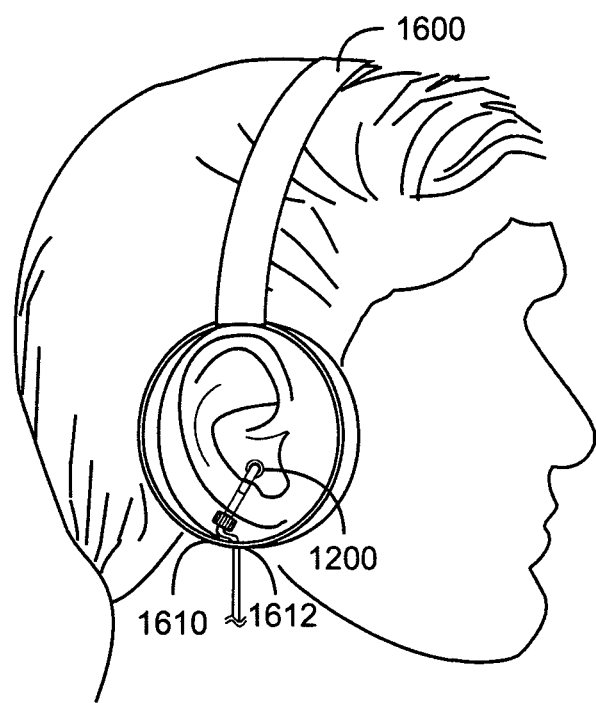

FIG. 16 illustrates a "headphone" 1600 support embodiment. In one embodiment (not shown), a headphone ear piece secures a concha body (FIGS. 8A-B) or an ear canal sensor (FIGS. 9A-B) by placement over the ear, in a similar manner as described with respect to FIGS. 14A-B. In another embodiment, the headphone 1600 provides a "ring-shaped" earpiece 1610 that provides a cable support 1612 for an ear clip sensor 1200, as shown.

FIGS. 17A-B illustrate a concha-clip ear sensor 1700 embodiment having a sensor body 1800, a connector 1710 and a sensor cable 1720 providing communications between the sensor body 1800 and the connector 1710. As described in further detail with respect to FIGS. 18A-E, the sensor body 1800 has resilient legs that are manually flexed so as to slide over an ear periphery and onto either side of a concha site. As described in further detail with respect to FIG. 19, the sensor body 1800 incorporates an optical assembly 1910 (FIG. 19) configured to transmit multiple wavelength light into the concha tissue and detect that light after attenuation by pulsatile blood flow within the concha tissue. In a particular embodiment, the sensor body 1800 has an emitter housing 1840 (FIGS. 18A-E) configured to fit inside the ear and a detector housing 1850 (FIGS. 18A-E) configured to fit outside the ear. In other embodiments, the sensor body is configured so as to place an emitter outside the ear and a detector inside the ear. In an embodiment, the sensor body 1800 is configured so that the sensor cable 1720 extends generally perpendicular to the sensor body 1800, as shown and described with respect to FIGS. 17-26. In another sensor body embodiment 2700 (FIGS. 27A-F) the sensor cable 1720 extends generally parallel to the sensor body, as described in further detail with respect to FIGS. 27A-E, below. Although the sensor body 1800, 2700 as described below has legs 1830 extending from a base 1810 so as to generally form a "U"-shape, the sensor body 1800, 2700 can be constructed of any of various resilient, pre-formed materials having a variety of shapes and sizes so as to attach to ear tissue, such as a concha site or ear lobe site.

FIGS. 18A-E further illustrate a sensor body 1800 having a base 1810, a strain relief 1820 formed at a side of the base 1810 and a pair of resilient legs 1830 extending from the base 1810. The strain relief 1820 has a cable aperture 1822 that accommodates the sensor cable 1720 (FIGS. 17A-B). An emitter housing 1840 extends from one leg 1830 and a detector housing 1850 extends from the other leg 1830. The legs 1830 accommodate cable conductors extending between the connector 1710 (FIGS. 17A-B) and an optical assembly 1910 (FIG. 19) located in the housings 1840, 1850. Each housing 1840, 1850 has an optical end 1842, 1852 (FIG. 20B) having an aperture 1844, 1854 (FIG. 20B) that passes light from the emitter housing 1840 to the detector housing 1850. In an embodiment, the housings 1840, 1850 fit on either side of a concha tissue site so that light is transmitted from an emitter 1916 (FIG. 19), through the concha tissue and received by a detector 1912 (FIG. 19), as described in detail below. In an embodiment, the emitter housing 1840 fits within the ear and the detector housing 1850 outside the ear. In an embodiment, a cup 1860 extends from the detector housing 1850. The cup 1860 has a generally circular edge and a curvature that accommodates the surface behind the ear. Accordingly, the cup 1860 advantageously provides a more comfortable and secure fit of the detector housing 1850 to the ear and further functions as a light shield, blocking external light sources from the detector 1912. The resilent legs 1830 are manually flexed so that the emitter housing 1840 is moved away from the detector housing 1850 so as to position the detector housing 1850 and emitter housing 1840 over opposite sides of a concha site. The legs are then released to an unflexed position so that the concha site is grasped between the detector housing 1850 and emitter housing 1840.

Figure 19:
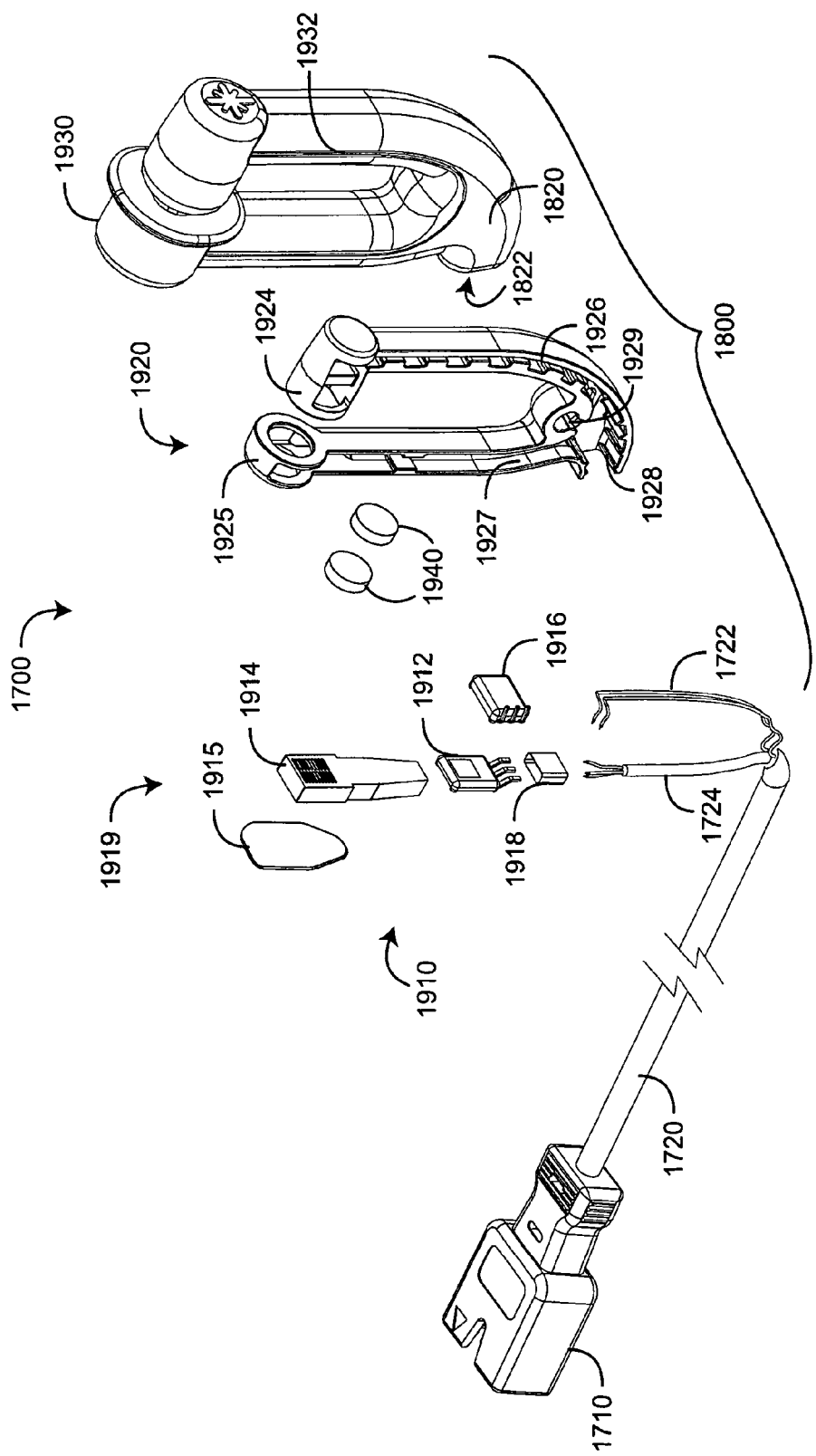
Figures 20A, 20B:
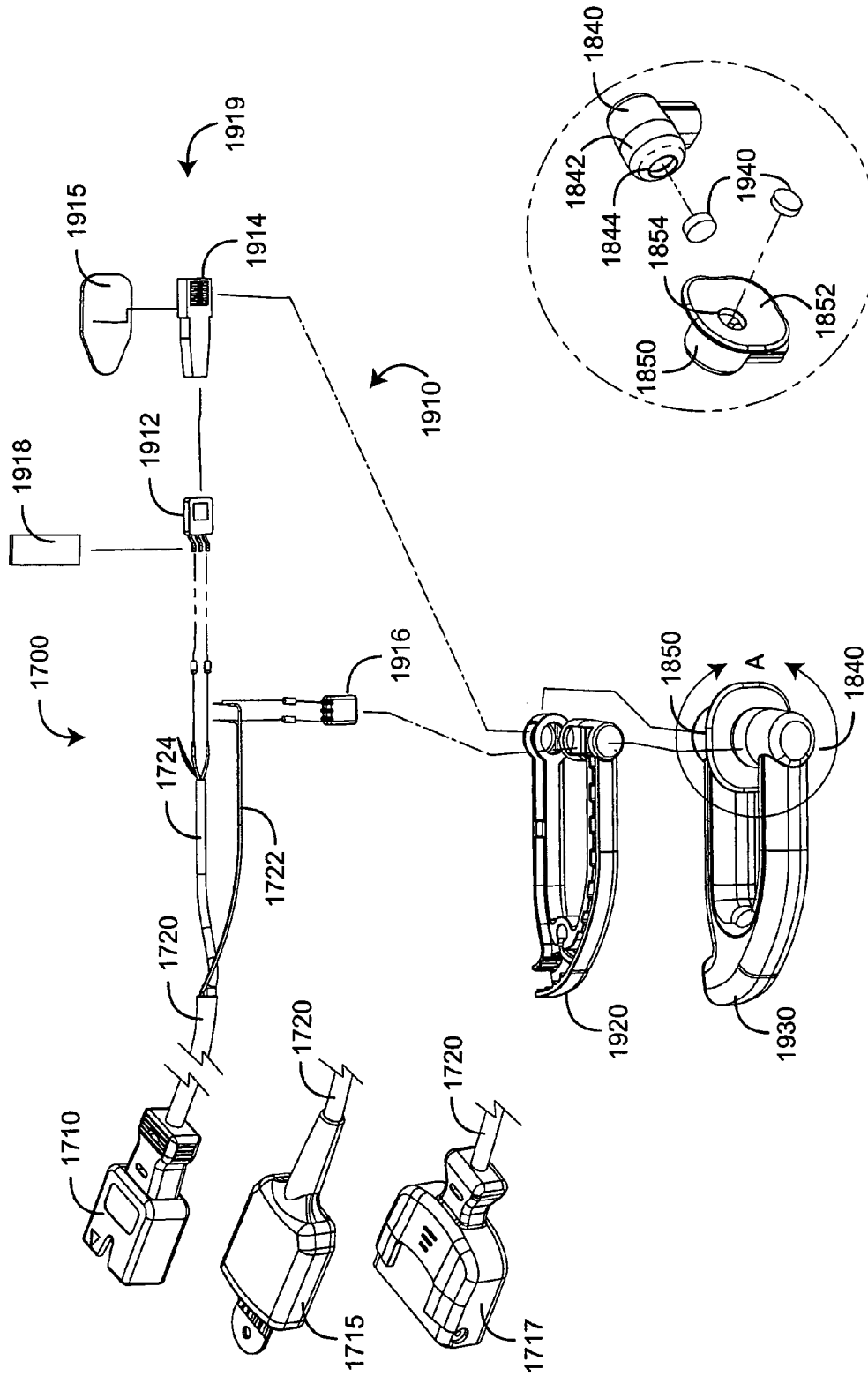
FIGS. 20A-B are assembly and detailed assembly views of a concha-clip sensor.

FIGS. 19-20 further illustrates a concha-clip ear sensor 1700 having a connector 1710 in communications with a sensor body 1800 via a sensor cable 1720. The sensor body 1800 has an optical assembly 1910, a resilient frame 1920, a sensor housing 1930 and lenses 1940. As shown in FIGS. 19-20, the optical assembly 1910 has a detector 1912, a detector shield 1914, a light barrier 1915, an emitter 1916 and white electrical tape 1918. The cable 1720 has emitter wires 1722 and detector wires 1724 that are soldered to the emitter 1916 and detector 1912, respectively, and communicate emitter drive signals and detector response signals to/from the connector 1710.

Also shown in FIGS. 19-20, the resilient frame 1920 has an emitter channel 1926 terminating at an emitter holder 1924, a detector channel 1927 terminating at a detector holder 1925, a strain relief 1928 and a frame hole 1929. The optical assembly 1910 fits within the resilient frame 1920. In particular, the emitter wires 1722 are disposed within the emitter channel 1926, the detector wires 1724 are disposed in the detector channel 1927, the emitter is disposed in the emitter holder 1924 and the detector 1912 and corresponding shield 1914 and light barrier 1915 are disposed in the detector holder 1925. In an embodiment, the sensor housing 1930 is a one piece silicon skin disposed over the resilient frame 1920 and the optical assembly 1910, as described with respect to FIGS. 24A-C, below. In an embodiment, the resilient frame 1920 is a polypropylene/santoprene blend. The lenses 1940 are disposed within housing apertures 1844, 1854. In an embodiment, the lenses 1940 are formed from a translucent silicone adhesive. In an alternative embodiment, the lenses 1940 are separately formed from clear silicone and glued into place with a translucent silicone adhesive.

Figure 21A:
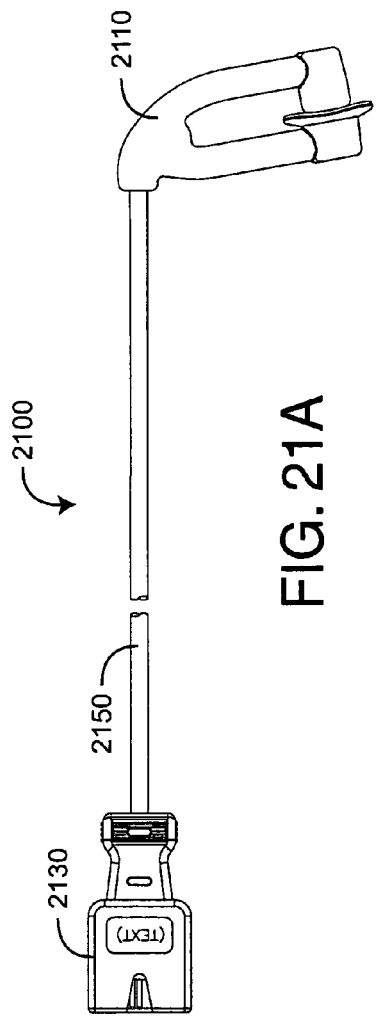
FIG. 21A-B are a mechanical representation and a corresponding electrical (schematic) representation of a concha-clip sensor having a DB9 connector.
Figure 21B:
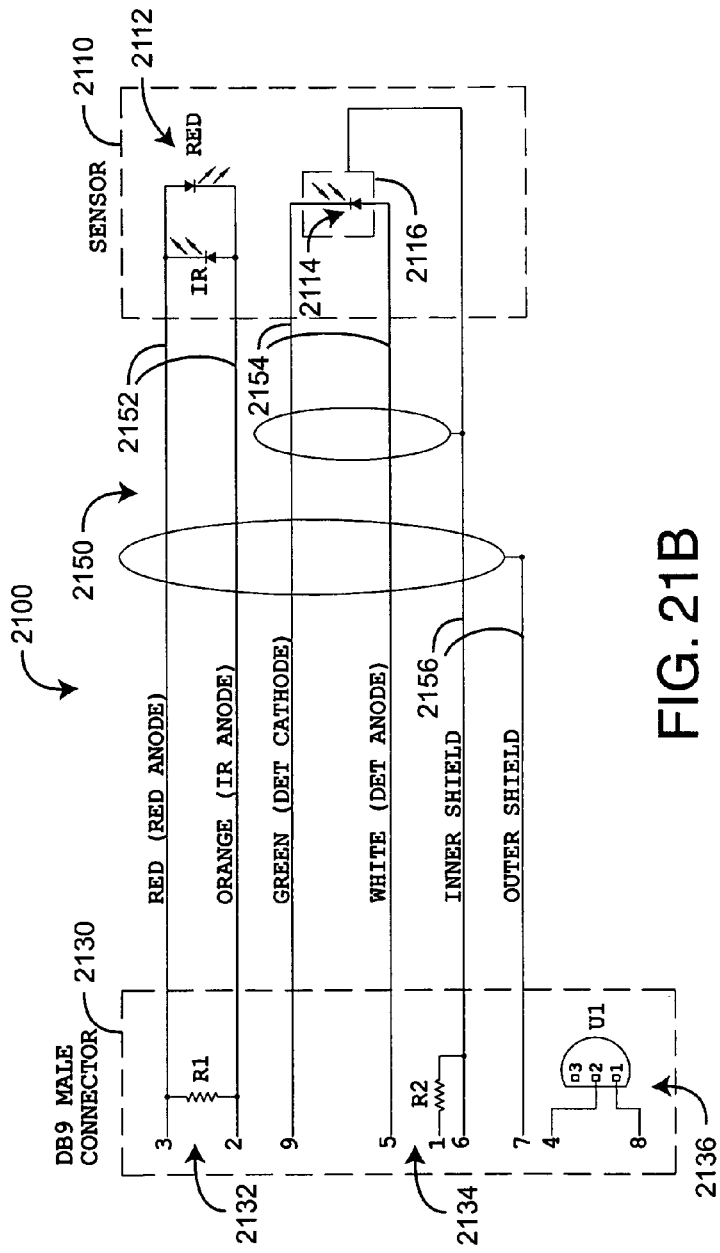
Figure 22A:
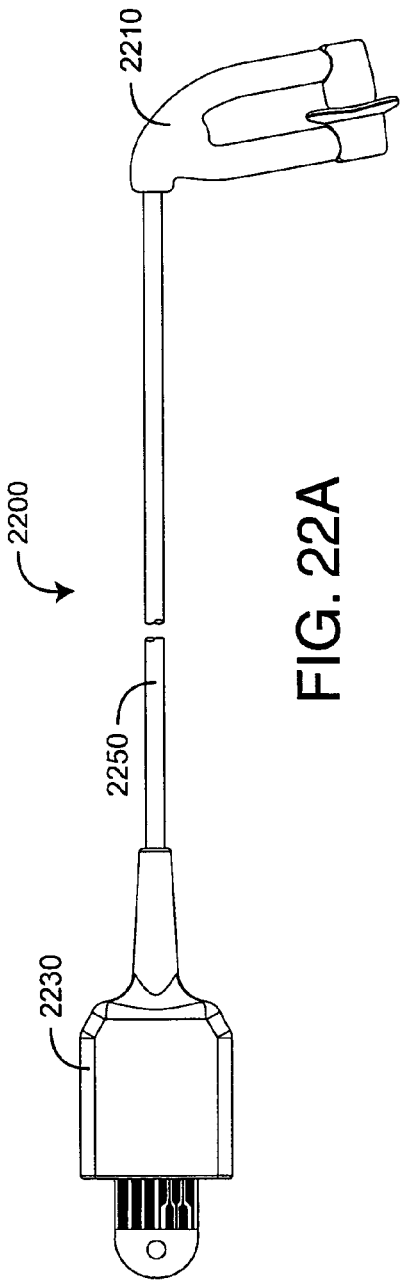
FIG. 22A-B are a mechanical representation and a corresponding electrical (schematic) representation of a concha-clip sensor having a MC8 connector.
Figure 22B:
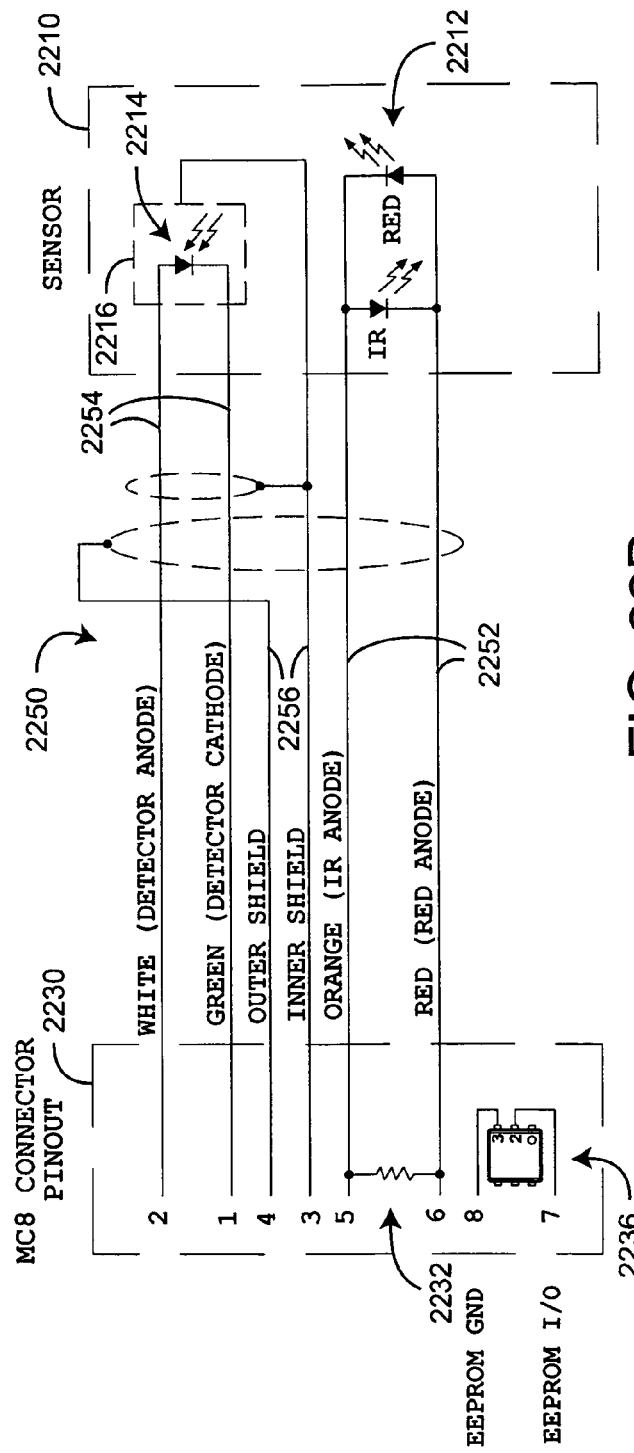

FIGS. 21-23 further illustrate concha-clip sensor embodiments 2100, 2200, 2300 having a DB9 connector 2130 (FIGS. 21A-B), a MC8 connector 2230 (FIGS. 22A-B) or a M15 connector 2330 (FIGS. 23A-B). The sensor bodies 2110, 2220, 2330 have red and IR emitters 2112, 2212, 2312 and detectors 2114, 2214; 2314 in communication with connectors 2130, 2230, 2330 via emitter wires 2152, 2252, 2352 and detector wires 2154, 2254, 2354. Sensor ID resistors 2132, 2232, 2332 are mounted in parallel with the emitters, and can be read by a monitor generating currents below the emitter-on thresholds. Compatibility resistors 2134, 2334 can be read by other monitor types. EEPROMs 2136, 2236, 2336 programmed with various sensor information can be read by more advanced monitors. Shield wires 2156, 2256, 2356 provide conductive paths via the connectors to a common shield ground. In an embodiment, ID resistors are 12.7 KΩ, compatibility resistors are 6.81 KΩ, and EEPROMs are 1-wire, 20K bit memories available from Maxim Integrated Products, Inc., Sunnyvale, Calif.

Figure 24A:
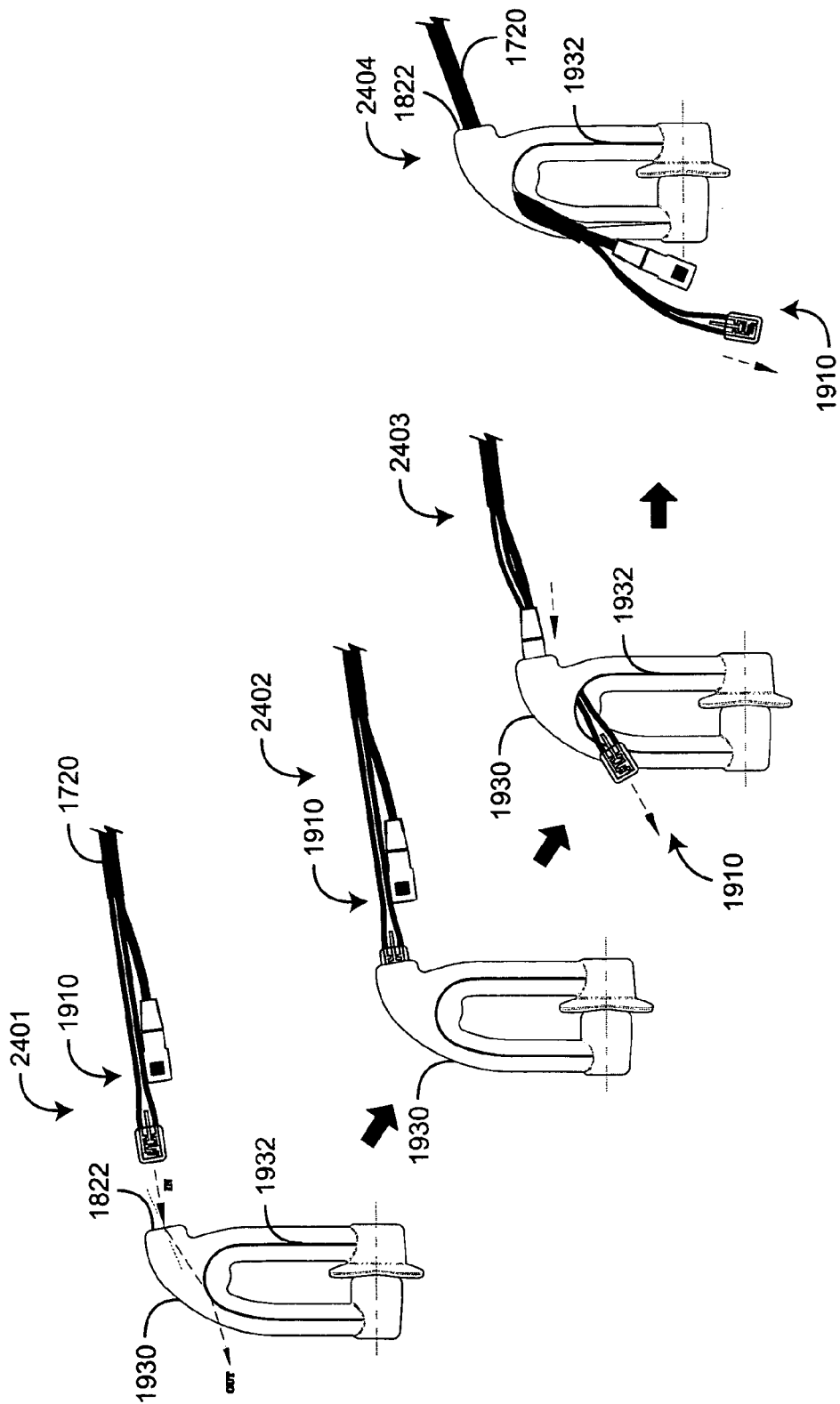
Figure 24C:
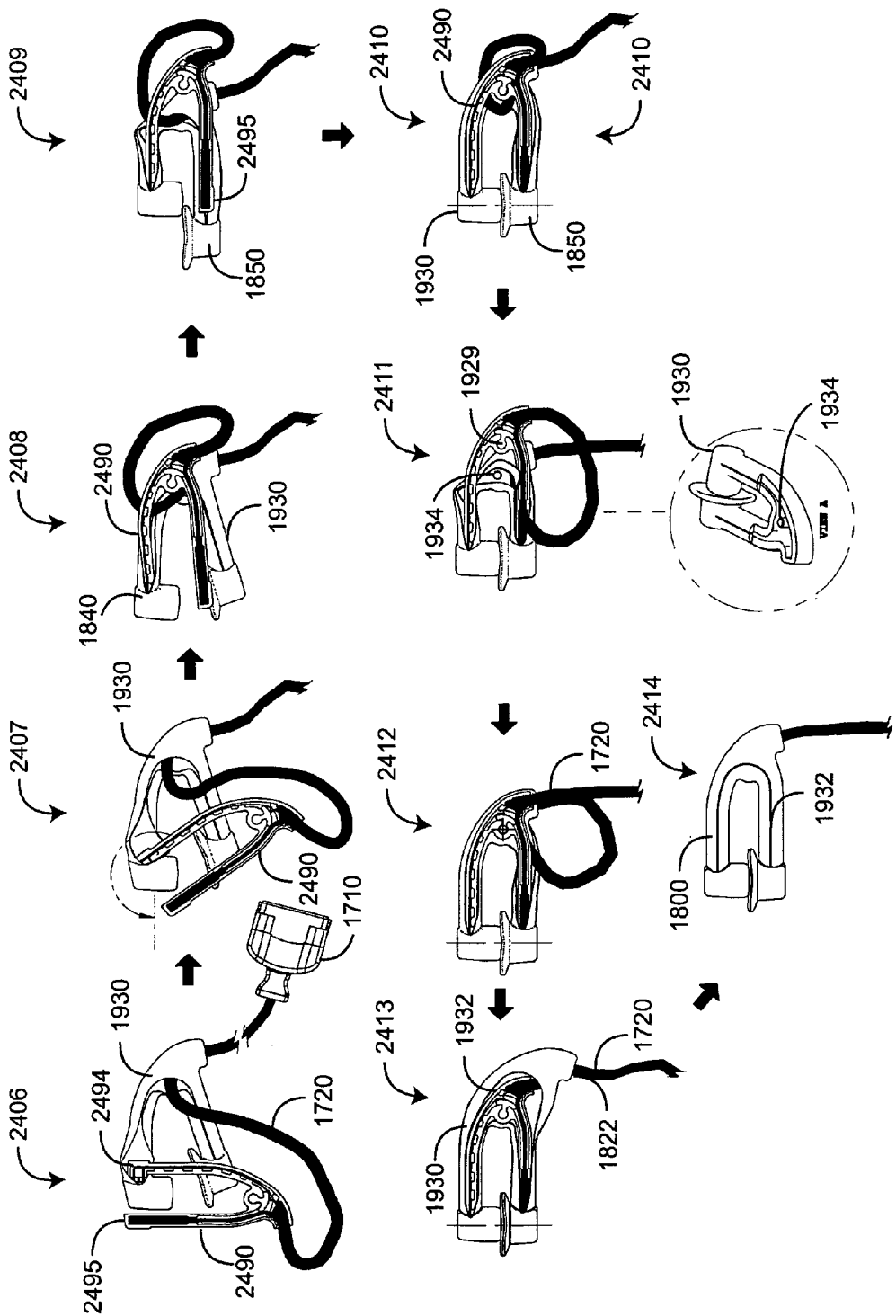
Figure 26B:
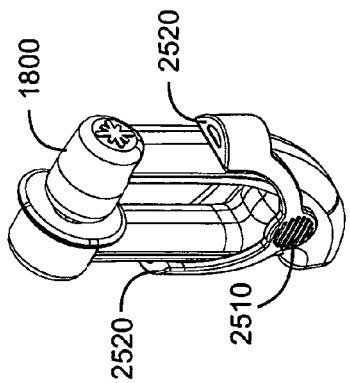
FIGS. 26A-F are top, disassembled perspective, assembled perspective, front, detector-side and emitter-side views of a concha-clip sensor body and corresponding force adjustment ring.
Figure 26C:
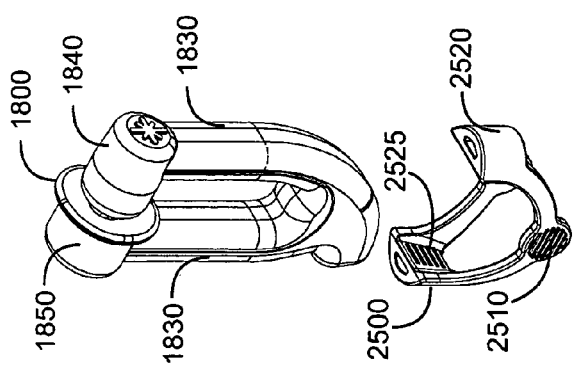
Figure 26A:
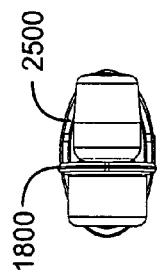
Figure 26E:
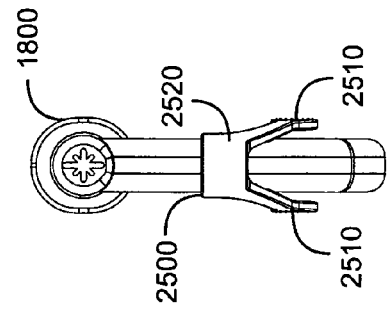
Figure 26F:
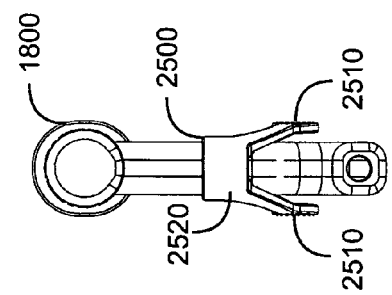
Figure 26D:
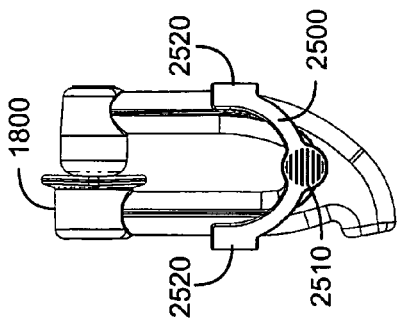

FIGS. 24A-C illustrate integration of the optical assembly 1910 disposed at the end of a sensor cable 1720, the resilient frame 1920 and the sensor housing 1930. As shown in FIG. 24A, the optical assembly 1910 is threaded into the sensor housing 1930. In particular, in a couple steps 2401-2402, the optical assembly 1910 is inserted into the sensor housing 1930 through the cable aperture 1822. In a further couple steps 2403-2404, the optical assembly 1910 and portions of the attached sensor cable 1720 are pulled through the cable aperture 1822 and out of a U-slot 1932 of the sensor housing 1930.

As shown in FIG. 24B, in a step 2405, the optical assembly 1910 is integrated with the resilient frame 1920 to form a frame assembly 2490. In particular, the detector assembly 1919 is inserted into a detector holder 1925 to form a framed detector 2495. Also, the emitter 1916 is inserted into an emitter holder 1924 to form a framed emitter 2495.

As shown in FIG. 24C, the frame assembly 2490 is integrated with the sensor housing 1930 to form the sensor body 1800. In several steps 2406-2408 the framed emitter 2494 is inserted into a pocket within the emitter housing 1840. In a couple additional steps 2409-2410, the framed detector 2495 is inserted into a pocket within the detector housing 1850. In a step 2411, a housing post 1934 is inserted into the frame hole 1929. In several additional steps 2412-2414, excess cable 1720 is removed from the sensor housing 1930 via the cable aperture 1822, and the U-slot 1932 is closed and sealed with an adhesive. The resulting sensor body 1800 is described in detail with respect to FIGS. 18A-E, above.

FIGS. 25-26 illustrate a force adjustment ring 2500 that slidably attaches to the sensor body 1800 so as to adjust the force of the sensor housings 1840, 1850 against concha tissue. The ring 2500 forms a generally oval opening 2526 having a pair of opposing sensor grips 2520 generally centered along a long axis of the opening 2526 and a pair of finger releases 2510 generally centered along a short axis of the opening 2526. The sensor grips 2520 have toothed faces 2525 configured to contact the sensor body legs 1830. The finger releases 2510 allow the ring to be squeezed between a finger and thumb, say, so as to compress the ring short axis, thereby lengthening the ring long axis and releasing the toothed faces 2525 from the legs 1830. In this manner, the ring 2500 can be positioned closer to or farther from the housings 1840, 1850 so as to increase or decrease the force on a concha tissue site.

FIGS. 27A-F illustrate an sensor body 2700 configured for a parallel-routed sensor cable, as compared with the sensor body 1800 (FIGS. 18A-E) configured for a perpendicular-routed sensor cable, as described above. The sensor body 2700 has a base 2710, a strain relief 2720 formed at a bottom end of the base 2710 and a pair of resilient legs 2730 extending from an opposite end of the base 2710. The strain relief 2720 has an aperture 2722 that accommodates the sensor cable 1720 (FIGS. 17A-B). An emitter housing 2740 extends from one leg 2730 and a detector housing 2750 extends from the other leg 2530. The legs 2730 accommodate cable conductors extending between a connector 1710 (FIGS. 17A-B) and an optical assembly 1910 (FIG. 19) located in the housings 2740, 2750. Each housing 2740, 2750 has an optical end having an aperture that passes light from the emitter housing 2740 to the detector housing 2750. In an embodiment, the housings 2740, 2750 fit on either side of a concha tissue site so that light is transmitted from an emitter of the optical assembly, through the concha tissue and received by a detector of the optical assembly. In an embodiment, the emitter housing 2740 fits within the ear and the detector housing outside the ear. In an embodiment, a cup 2760 extends from the optical end of the detector housing 2750. The cup 2760 has a generally circular edge and a curvature that accommodates the outside curvature of the ear. Accordingly, the cup 2760 advantageously provides a more comfortable and secure fit of the detector housing 2750 to the ear and further functions as a light shield, blocking external light sources from the detector assembly.

A sensor body 1800 (FIGS. 18A-E), 2700 (FIGS. 27A-F) is described above with respect to directly flexing resilient legs in order to space apart emitter and detector housings for placement on a concha site. In another embodiment, a pair of finger levers can extend from the legs to a position below the sensor body base opposite the resilient legs. The finger levers can be squeezed between finger and thumb so as to flex the resilient legs for concha site placement.

In a particular advantageous embodiment, a single finger lever can extend from one leg to a position below the base. This single finger lever can be squeezed using a sensor cable portion extending from the sensor body base for leverage. Such a single finger lever configuration eliminates potential discomfort from a second lever poking a patient's neck area.

An ear sensor has been disclosed in detail in connection with various embodiments. These embodiments are disclosed by way of examples only and are not to be construed as limiting the scope of the claims that follow. One of ordinary skill in art will appreciate many variations and modifications.

What is claimed is:

1. An ear sensor for optically measuring physiological parameters related to blood constituents by transmitting multiple wavelengths of light into a concha site and receiving the light after attenuation by pulsatile blood flow within the concha site, the ear sensor comprising a sensor body, a sensor connector and a sensor cable interconnecting the sensor body and the sensor connector, the sensor body comprising:
    a base;
    a first leg extending from the base to a detector housing;
    a second leg extending from the base to an emitter housing;
    an optical assembly having an emitter and a detector, the emitter disposed in the emitter housing, and the detector disposed in the detector housing; and
    a cup extending from the detector housing, wherein the cup generally conforms to the curvature of a concha site.

2. The ear sensor according to claim 1, further comprising:
    a resilient frame; and
    a one piece molded skin disposed over the resilient frame.

3. The ear sensor according to claim 1, wherein in an unflexed position the emitter housing is proximate the detector housing and in a flexed position the emitter housing is distal the detector housing, wherein the legs are configured to be moved to the flexed position so as to position the detector housing and emitter housing over opposite sides of the concha site, and wherein the legs are configured to be released to the unflexed position so that the concha site is grasped between the detector housing and emitter housing.

4. The ear sensor according to claim 3, further comprising:
    a sensor cable having a first end and a second end;
    a plurality of wires disposed within the sensor cable;
    the wires extending from the first end of the sensor cable and disposed within a plurality of channels defined by the resilient frame;
    the wires electrically and mechanically attached to the optical assembly;
    a connector attached to a second end of the sensor cable; and
    the wires electrically and mechanically attached to the connector so as to provide communications between the connector and the optical assembly.

5. The ear sensor according to claim 4, further comprising a stabilizer that maintains the position of the detector housing and the emitter housing on the concha site.

6. The ear sensor according to claim 5, wherein the stabilizer comprises:
    a ring that encircles the legs, the ring having a hold position disposed against the legs and a release position spaced from the legs; and
    a release that, when pressed, moves the ring from the hold position to the release position, allowing the ring to slidably move along the legs in a direction away from the base so as to increase the force of the emitter housing and detector housing on the concha site in the hold position and in a direction toward the base so as to decrease the force of the emitter housing and the detector housing on the concha site in the hold position.

7. The ear sensor according to claim 6, wherein the stabilizer further comprises an ear hanger configured to rest along the back of an ear and couple to at least one of the legs and the sensor cable.

8. The ear sensor according to claim 1, wherein the cup has a generally circular edge.

9. An ear sensor method comprising:
    providing a sensor body having a base, legs extending from the base and an optical housing disposed at ends of the legs distal the base;
    disposing an optical assembly in the housing;
    providing an ear surface conforming member coupled to at least a portion of the housing so as to physically couple the housing to a concha site and block ambient light from the optical assembly accordingly, the ear surface conforming member having a cup shape.

10. The ear sensor method according to claim 9, wherein the housing is configured such that the force of the housing against the concha site is adjustable.

11. The ear sensor method according to claim 10, wherein the force of the housing against the concha site is configured to be adjusted by positioning a force adjustment ring on the sensor body so as to encircle the legs.

12. The ear sensor method according to claim 11, wherein positioning comprises:
    squeezing a ring release so as to move ring grips away from the legs;
    moving the force adjustment ring along the legs and toward the housing so as to increase the force of the housing on the concha site; and
    moving the force adjustment ring along the legs and away from the housing so as to decrease the force of the housing on the concha site.

13. The ear sensor method according to claim 9, further comprising providing a support that supports at least a portion of the weight of the sensor body and corresponding sensor cable so as to reduce the force needed to attach the housing to the concha site.

14. The ear sensor method according to claim 13, wherein the support comprises an ear hook attached to at least one of the sensor body and sensor cable and configured to be placed over an ear.

15. The ear sensor method according to claim 9, wherein the sensor body has a flexed position and an unflexed position, wherein in the flexed position the housing is configured to be placed over the concha site, and wherein in an unflexed position the housing is configured to be attached to the concha site and position the optical assembly to illuminate the concha site.

16. The ear sensor method according to claim 9, wherein the ear surface conforming member has a generally circular edge.

17. An ear sensor comprising:
- a clip means for clipping on a concha site, the clip means having a flexed position and an unflexed position;
- an optical means for transmitting multiple wavelength light into a tissue site when activated and for receiving the light after attenuation by pulsatile blood flow within the tissue site, the optical means disposed on the clip means so that the optical means can be positioned on the concha site in the flexed position and pinched against the concha site in the unflexed position;
- a cup means for physically coupling at least a portion of the optical means to the concha site and for blocking ambient light from the optical means;
- a connector means for mechanically attaching to and electrically communicating with a monitor; and
- a cable means for interconnecting the connector means with the optical means.

18. The ear sensor according to claim 17, wherein the clip means comprises a resilient frame means for securing the optical means in a fixed position relative to the tissue site.

19. The ear sensor according to claim 18, further comprising a skin means for enclosing the resilient frame means and the optical means.

20. The ear sensor according to claim 19, further comprising an adjustable force means for holding the clip means to the concha site.

21. The ear sensor according to claim 19, further comprising a support means for holding the clip means to the concha site.

22. The ear sensor according to claim 17, wherein the cup means has a generally circular edge.

* * * * *